(12) United States Patent
Shraga

(10) Patent No.: US 7,105,006 B2
(45) Date of Patent: Sep. 12, 2006

(54) ADJUSTABLE LANCET DEVICE AND METHOD

(75) Inventor: Steven Shraga, Surfside, FL (US)

(73) Assignee: Stat Medical Devices, Inc., Miami, FL (US)

( * ) Notice: Subject to any disclaimer, the term of this patent is extended or adjusted under 35 U.S.C. 154(b) by 194 days.

(21) Appl. No.: 10/641,101

(22) Filed: Aug. 15, 2003

(65) Prior Publication Data

(51) Int. Cl.
A61B 17/32 (2006.01)
(52) U.S. Cl. .................................. 606/182; 606/172
(58) Field of Classification Search ............. 606/182, 606/181, 172
See application file for complete search history.

(56) References Cited

U.S. PATENT DOCUMENTS

| | | |
|---|---|---|
| 676,678 A | 6/1901 | Ellifrits |
| 1,135,465 A | 4/1915 | Pollock |
| 2,823,677 A | 2/1958 | Hein, Jr. |
| 2,848,809 A | 8/1958 | Crowder |
| 3,589,213 A | 6/1971 | Gourley |
| 3,760,809 A | 9/1973 | Campbell, Jr. |
| 4,064,871 A | 12/1977 | Reno |
| 4,139,011 A | 2/1979 | Benoit et al. |
| 4,157,086 A | 6/1979 | Maiorano et al. |
| 4,203,446 A | 5/1980 | Höfert et al. |
| 4,257,561 A | 3/1981 | McKinney |
| 4,388,925 A | 6/1983 | Burns |
| 4,426,105 A | 1/1984 | Plaquin et al. |
| 4,438,770 A | 3/1984 | Unger et al. |
| 4,449,529 A | 5/1984 | Burns et al. |
| 4,469,110 A | 9/1984 | Slama |
| 4,517,978 A | 5/1985 | Levin et al. |
| 4,527,561 A | 7/1985 | Burns |
| 4,539,988 A | 9/1985 | Shirley et al. |
| 4,553,541 A | 11/1985 | Burns |
| 4,628,929 A | 12/1986 | Intengan et al. |
| 4,643,189 A | 2/1987 | Mintz |
| 4,785,858 A | 11/1988 | Valentini et al. |
| RE32,922 E | 5/1989 | Levin et al. |
| 4,834,667 A | 5/1989 | Fowler et al. |

(Continued)

FOREIGN PATENT DOCUMENTS

CA          523078          3/1956

(Continued)

OTHER PUBLICATIONS

Sutor et al., "Bleeding from Standardized Skin Punctures: Automated Technic for Recording Time, Intensity, and Pattern of Bleeding", A.J.C.P., vol. 55, pp. 541-549 (May 1971).

Primary Examiner—Corrine McDermott
Assistant Examiner—Christopher Prone
(74) Attorney, Agent, or Firm—Greenblum & Bernstein, P.L.C.

(57) ABSTRACT

Lancet device that includes a body. A trigger is mounted to the body. A front cover has a skin engaging end that includes a lancet opening through which a lancet needle extends. A holding member is movably mounted within the body and includes a front end a rear end. The front end can be configured to receive a lancet. A stop surface moves with the holding member. A cam wheel includes cam surfaces which can be contacted by the stop surface. The cam wheel is configured to rotate at least partially. The cam wheel rotates about an axis that is parallel to an axis running through at least one of the lancet opening and the holding member.

44 Claims, 17 Drawing Sheets

U.S. PATENT DOCUMENTS

| | | | |
|---|---|---|---|
| 4,858,607 A | 8/1989 | Jordan et al. | |
| 4,869,249 A | 9/1989 | Crossman et al. | |
| 4,895,147 A | 1/1990 | Bodicky et al. | |
| 4,924,879 A | 5/1990 | O'Brien | |
| 4,976,724 A | 12/1990 | Nieto et al. | |
| 4,990,154 A | 2/1991 | Brown et al. | |
| 5,074,872 A | 12/1991 | Brown et al. | |
| 5,133,730 A | 7/1992 | Biro et al. | |
| 5,147,375 A | 9/1992 | Sullivan et al. | |
| 5,196,025 A * | 3/1993 | Ranalletta et al. | 606/182 |
| 5,212,879 A | 5/1993 | Biro et al. | |
| 5,269,799 A | 12/1993 | Daniel | |
| 5,282,822 A | 2/1994 | Macors et al. | |
| 5,304,193 A * | 4/1994 | Zhadanov | 606/182 |
| 5,314,441 A | 5/1994 | Cusack et al. | |
| 5,318,584 A | 6/1994 | Lange et al. | |
| 5,324,303 A | 6/1994 | Strong et al. | |
| 5,350,392 A | 9/1994 | Purcell et al. | |
| 5,356,420 A | 10/1994 | Czernecki et al. | |
| 5,366,470 A | 11/1994 | Ramel | |
| 5,395,388 A | 3/1995 | Schraga | |
| 5,423,847 A | 6/1995 | Strong et al. | |
| 5,439,473 A | 8/1995 | Jorgensen | |
| 5,454,828 A | 10/1995 | Schraga | |
| 5,464,418 A | 11/1995 | Schraga | |
| 5,476,101 A | 12/1995 | Schramm et al. | |
| 5,509,345 A | 4/1996 | Cyktich | |
| 5,518,004 A | 5/1996 | Schraga | |
| 5,527,333 A | 6/1996 | Nikkels et al. | |
| 5,527,334 A | 6/1996 | Kanner et al. | |
| 5,529,581 A | 6/1996 | Cusack | |
| 5,545,174 A | 8/1996 | Schenk et al. | |
| 5,554,166 A * | 9/1996 | Lange et al. | 606/182 |
| 5,569,286 A | 10/1996 | Peckham et al. | |
| 5,569,287 A | 10/1996 | Tezuka et al. | |
| 5,571,132 A | 11/1996 | Mawhirt et al. | |
| D376,203 S | 12/1996 | Schraga | |
| 5,613,978 A * | 3/1997 | Harding | 606/181 |
| 5,628,764 A | 5/1997 | Schraga | |
| 5,628,765 A | 5/1997 | Morita | |
| 5,643,306 A | 7/1997 | Schraga | |
| 5,662,672 A | 9/1997 | Pambianchi et al. | |
| 5,730,753 A * | 3/1998 | Morita | 606/181 |
| 5,733,300 A | 3/1998 | Pambianchi et al. | |
| 5,741,288 A | 4/1998 | Rife | |
| RE35,803 E | 5/1998 | Lange et al. | |
| 5,772,677 A | 6/1998 | Mawhirt et al. | |
| 5,797,940 A | 8/1998 | Mawhirt et al. | |
| 5,797,942 A | 8/1998 | Schraga | |
| 5,873,887 A | 2/1999 | King et al. | |
| 5,879,367 A | 3/1999 | Latterell et al. | |
| 5,908,434 A | 6/1999 | Schraga | |
| 5,916,230 A * | 6/1999 | Brenneman et al. | 606/172 |
| 5,984,940 A | 11/1999 | Davis et al. | |
| 6,010,519 A | 1/2000 | Mawhirt et al. | |
| 6,022,366 A | 2/2000 | Schraga | |
| 6,042,595 A | 3/2000 | Morita | |
| 6,045,567 A | 4/2000 | Taylor et al. | |
| 6,056,765 A | 5/2000 | Bajaj et al. | |
| 6,071,294 A | 6/2000 | Simons et al. | |
| D428,150 S | 7/2000 | Ruf et al. | |
| 6,136,013 A | 10/2000 | Marshall et al. | |
| 6,152,942 A | 11/2000 | Brenneman et al. | |
| 6,156,050 A | 12/2000 | Davis et al. | |
| 6,156,051 A | 12/2000 | Schraga | |
| 6,168,606 B1 | 1/2001 | Levin et al. | |
| 6,183,489 B1 | 2/2001 | Douglas et al. | |
| 6,190,398 B1 | 2/2001 | Schraga | |
| 6,192,891 B1 | 2/2001 | Gravel et al. | |
| 6,197,040 B1 | 3/2001 | Le Vaughn et al. | |
| 6,210,420 B1 | 4/2001 | Mauze et al. | |
| 6,221,089 B1 | 4/2001 | Mawhirt | |
| 6,228,100 B1 | 5/2001 | Schraga | |
| 6,258,112 B1 | 7/2001 | Schraga | |
| 6,283,982 B1 | 9/2001 | Levaughn et al. | |
| 6,306,152 B1 | 10/2001 | Verdonk et al. | |
| 6,322,574 B1 | 11/2001 | Lloyd et al. | |
| 6,322,575 B1 | 11/2001 | Schraga | |
| 6,332,871 B1 | 12/2001 | Douglas et al. | |
| 6,346,114 B1 | 2/2002 | Schraga | |
| 6,358,265 B1 | 3/2002 | Thorne, Jr. et al. | |
| 6,364,889 B1 | 4/2002 | Kheiri et al. | |
| 6,379,317 B1 | 4/2002 | Kintzig et al. | |
| 6,395,495 B1 | 5/2002 | Montagnier et al. | |
| 6,409,740 B1 | 6/2002 | Kuhr et al. | |
| 6,419,661 B1 | 7/2002 | Kuhr et al. | |
| 6,451,040 B1 | 9/2002 | Purcell | |
| 6,464,649 B1 | 10/2002 | Duchon et al. | |
| 6,506,168 B1 | 1/2003 | Fathallah et al. | |
| 6,514,270 B1 | 2/2003 | Schraga | |
| 6,540,762 B1 | 4/2003 | Bertling | |
| 6,558,402 B1 * | 5/2003 | Chelak et al. | 606/182 |
| 2003/0028126 A1 * | 2/2003 | List | 600/583 |
| 2003/0187470 A1 * | 10/2003 | Chelak et al. | 606/182 |

FOREIGN PATENT DOCUMENTS

| | | | |
|---|---|---|---|
| CA | 2314859 | * | 2/2001 |
| EP | 0061102 | | 9/1982 |
| EP | 0137975 | | 4/1985 |
| EP | 0189117 | | 7/1986 |
| EP | 0885590 | | 12/1998 |
| EP | 0904731 | | 3/1999 |
| EP | 1074219 | | 2/2001 |
| FR | 1126718 | | 11/1956 |

* cited by examiner

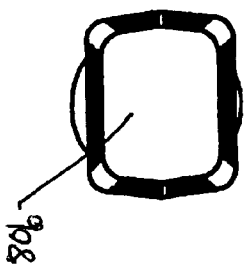
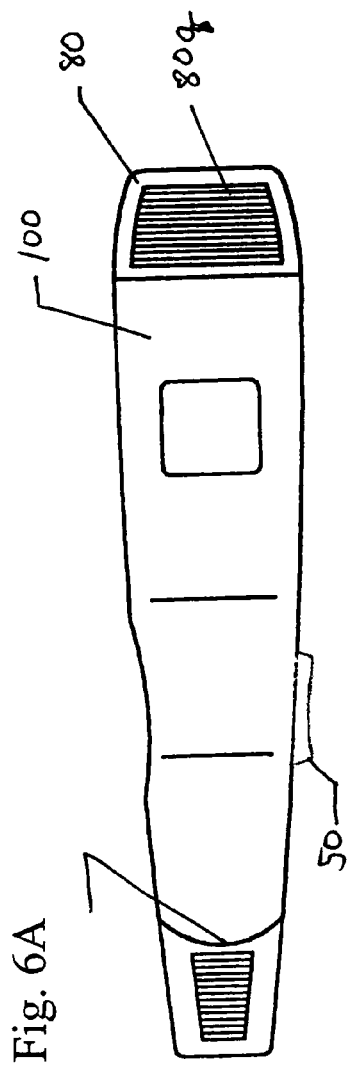
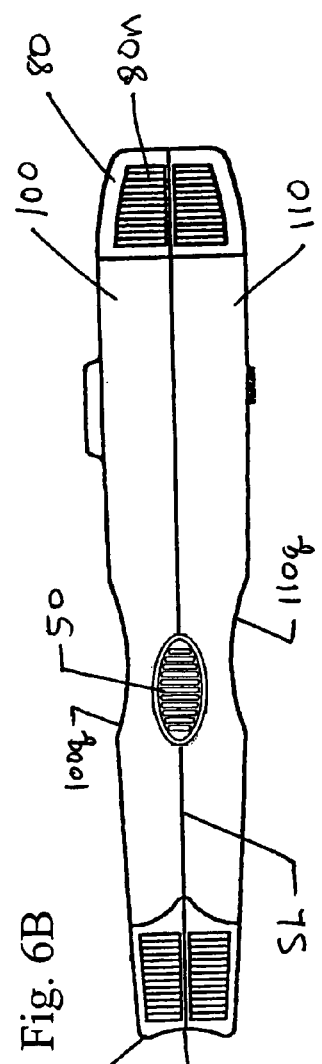
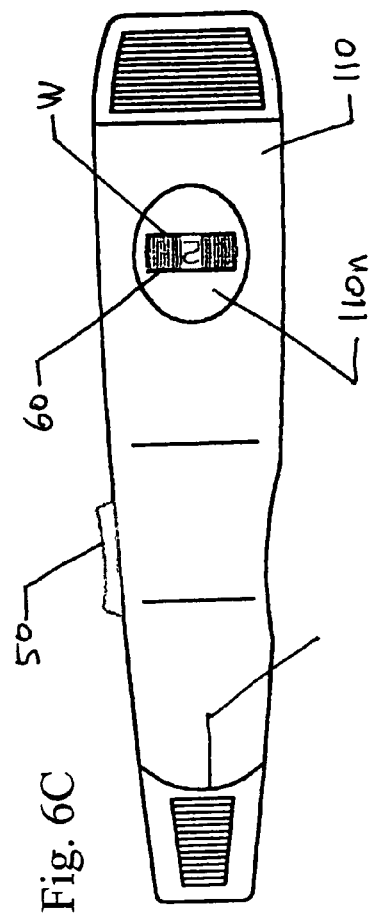
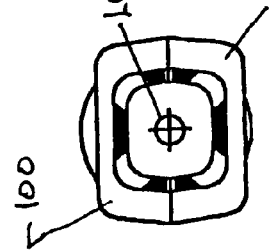

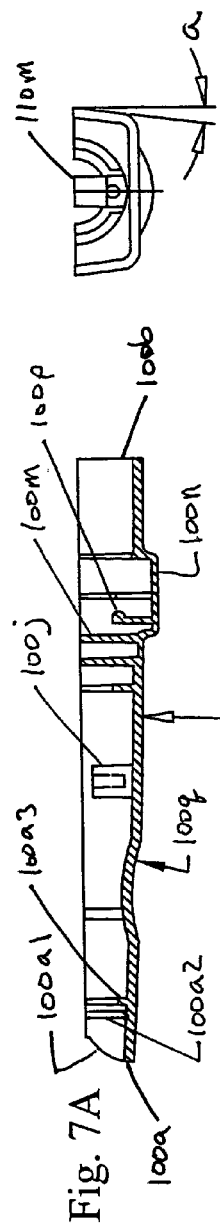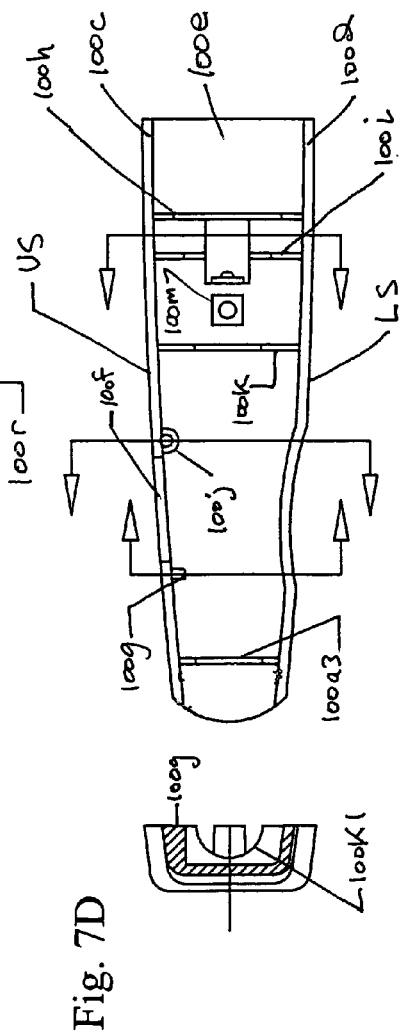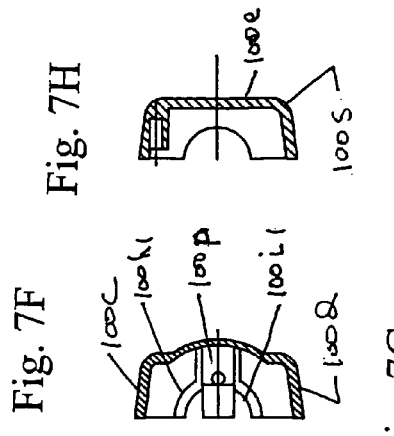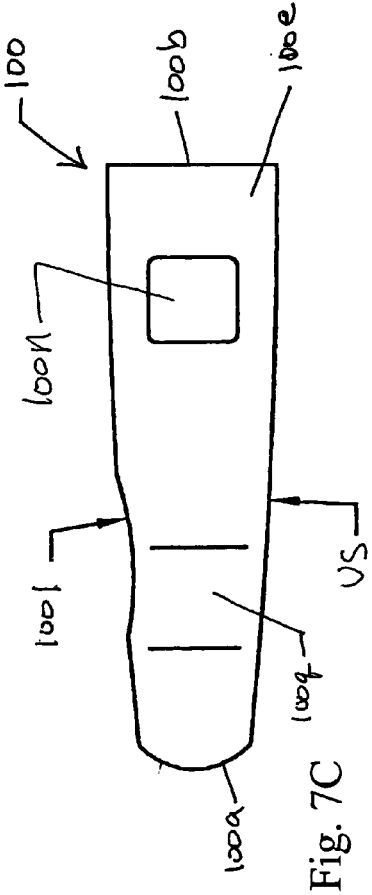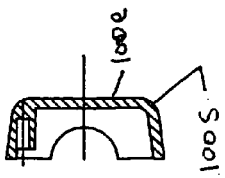

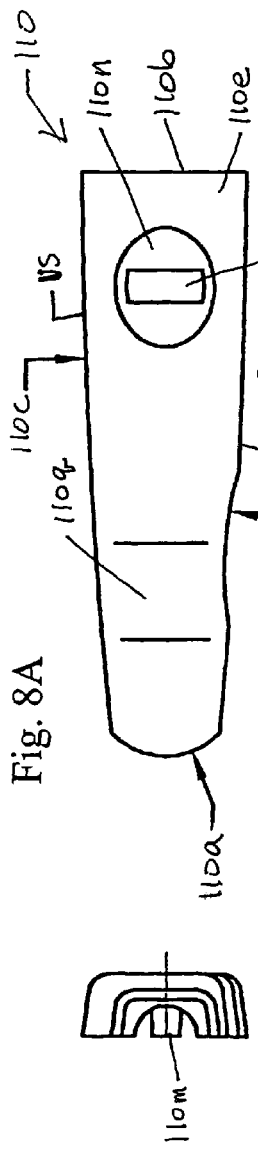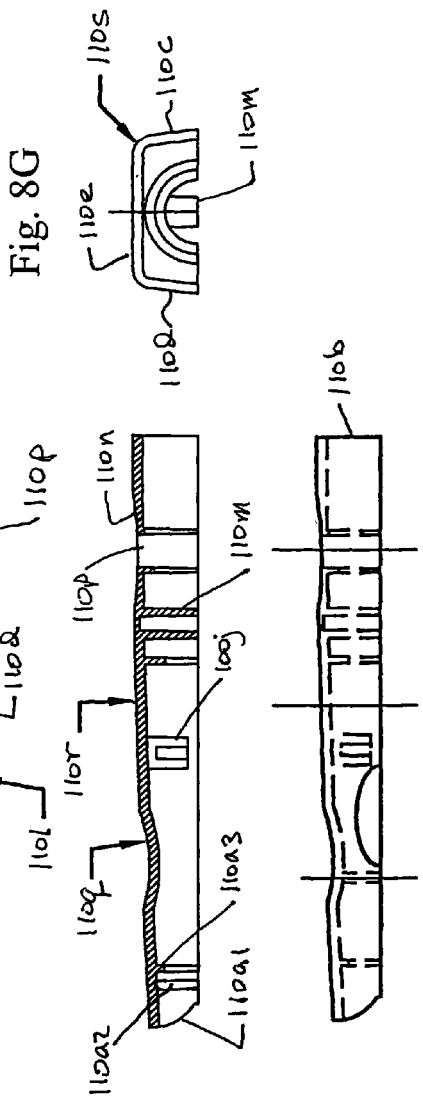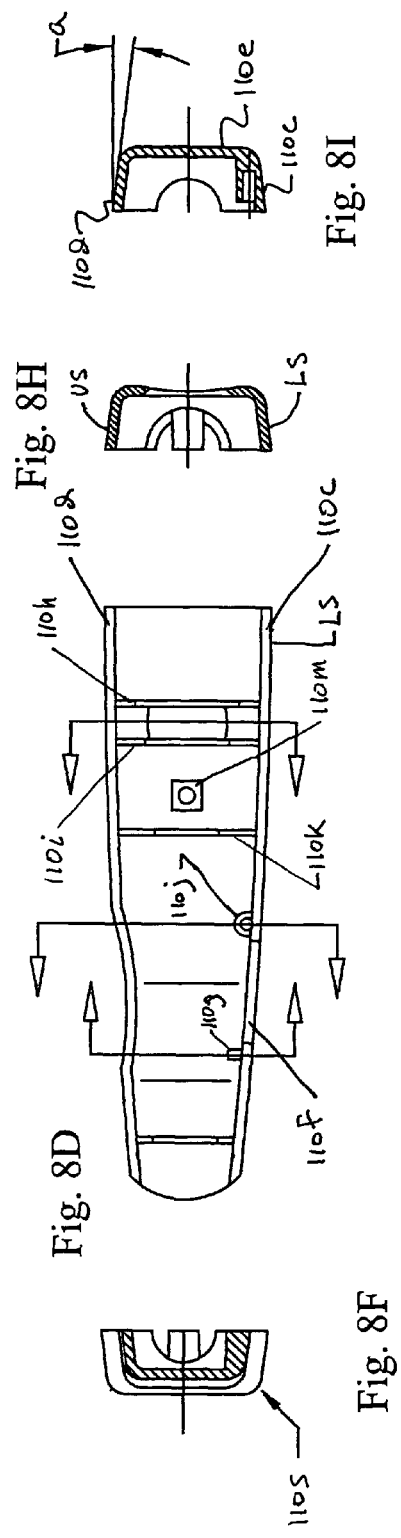

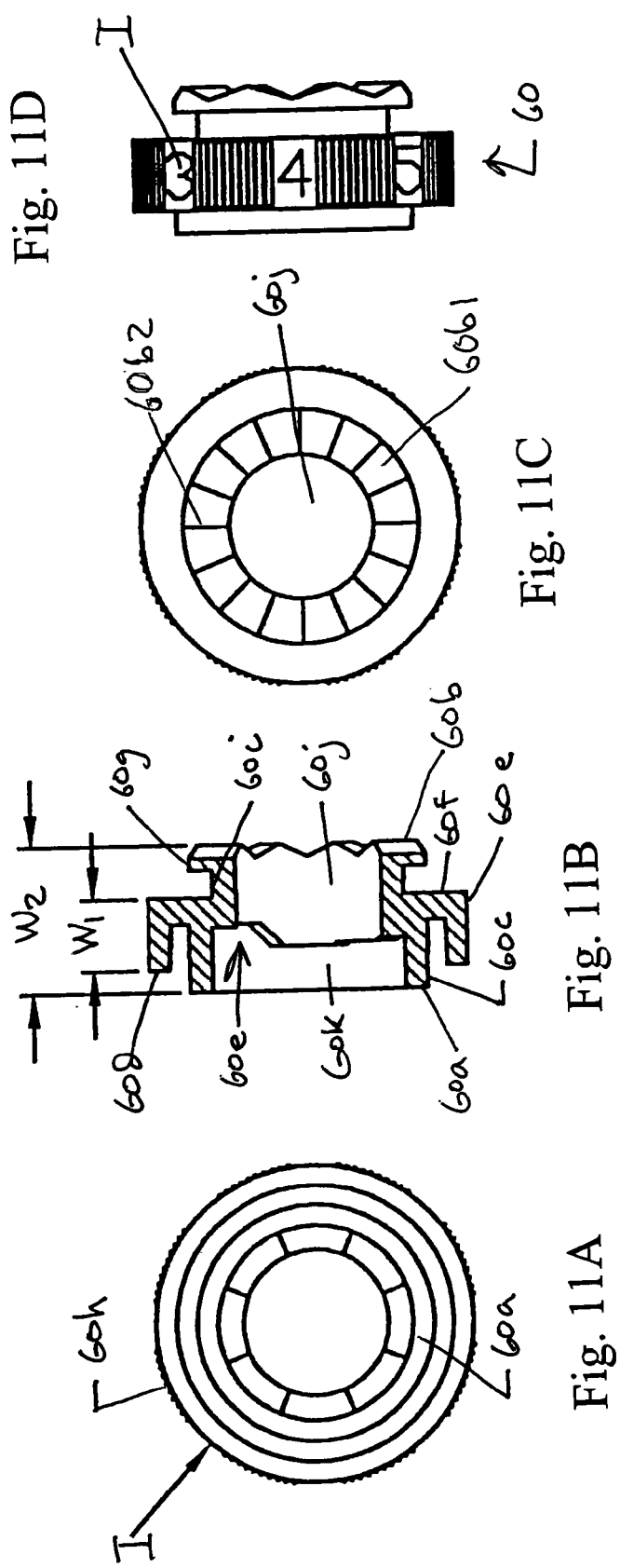

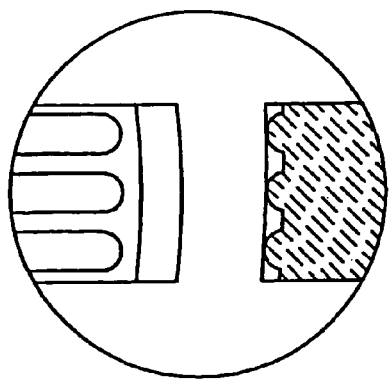
Fig. 17G
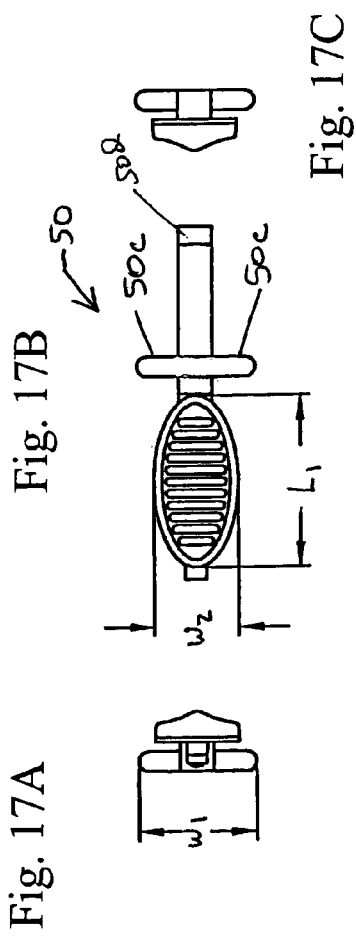
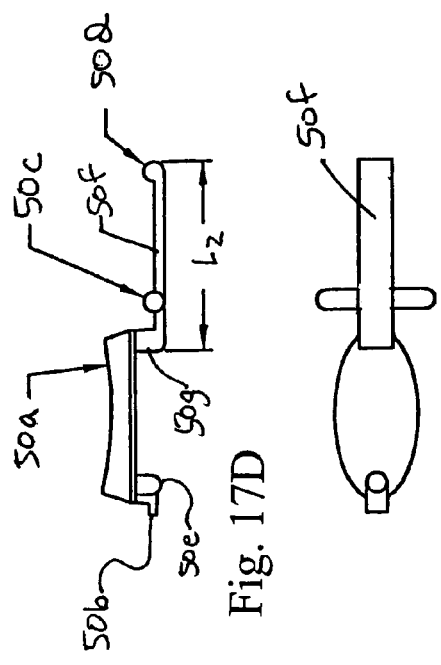
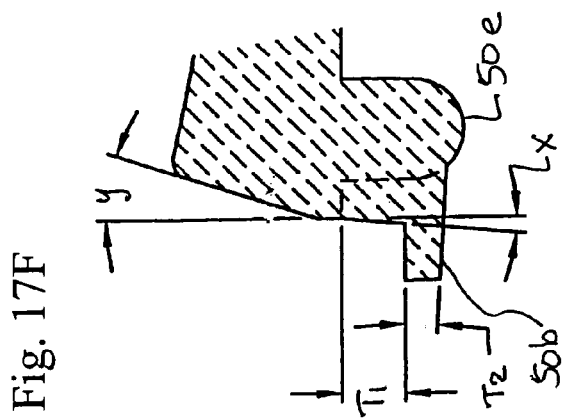

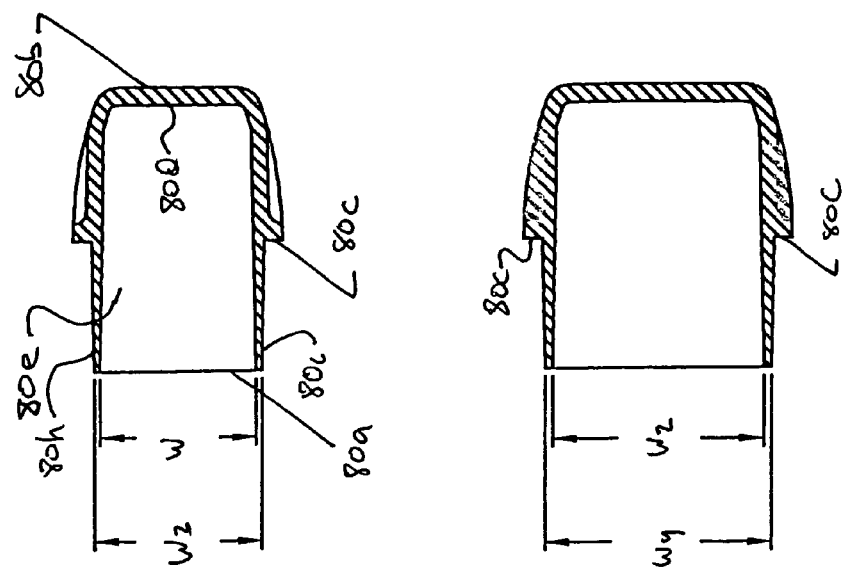
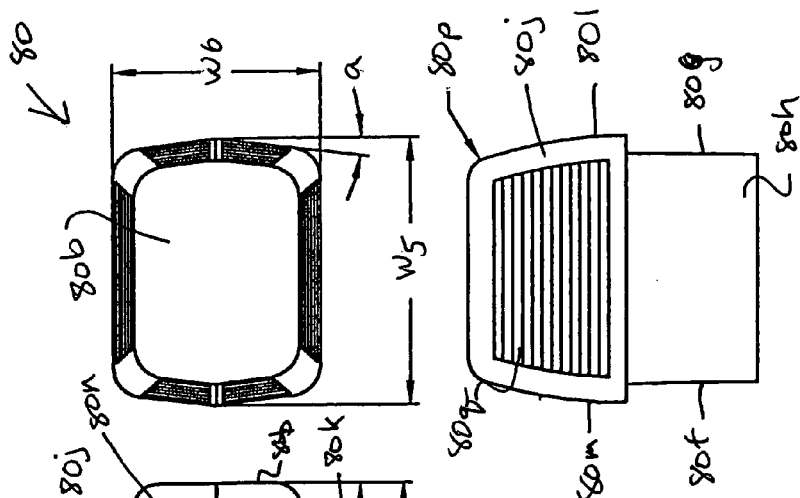

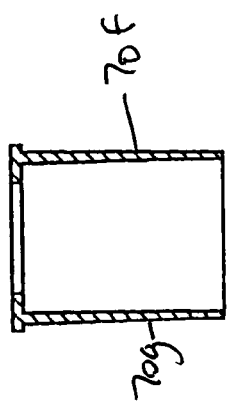
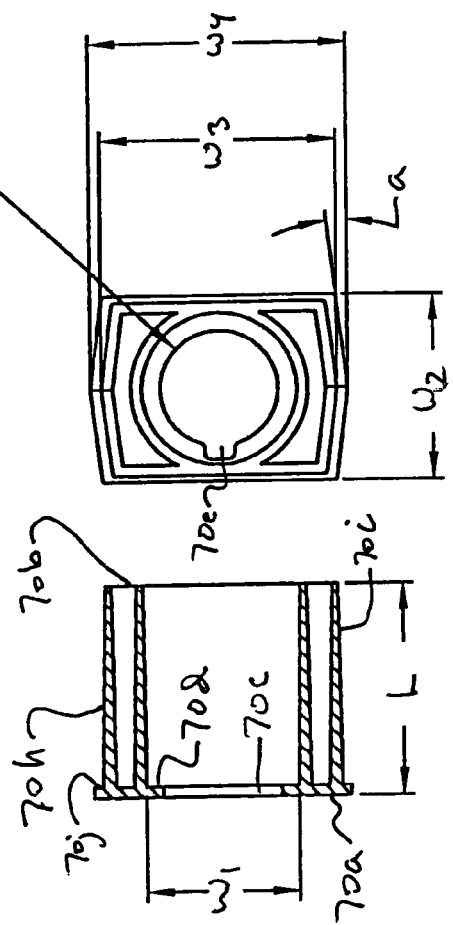
Fig. 19C
Fig. 19B
Fig. 19A

ADJUSTABLE LANCET DEVICE AND METHOD

BACKGROUND OF THE INVENTION

1. Field of the Invention

The invention relates to a lancet device having an adjusting capability, and a method of using a lancet device. In particular, the invention relates to a lancet device which utilizes an adjustable depth penetration. Lancet devices are used to penetrate and puncture the skin in order to allow the taking of a blood sample for testing. The present device allows the user to control the depth of this penetration by a simple adjustment mechanism.

2. Discussion of Background Information

Lancet devices are commonly used to prick the skin of the user so that one or more drops of blood may be extracted for testing. Some users, such as diabetics, for example, may have to test their blood sugar levels several times a day. This may be accomplished by the user using a simple needle. However, this procedure is often problematic for the user since the needle may be difficult to handle. Moreover, controlling the depth of penetration cannot be reliably accomplished without the use of a mechanical device. Additionally, many users simply cannot perform the procedure owing to either a fear of needles or because they lack a steady hand. As a result, lancet devices have been developed which allow the user to more easily and reliably perform this procedure.

Most lancet devices lack convenient and flexible adjustability. Such devices are typically made adjustable by switching their tips. U.S. Pat. No. Re. 32,922 to LEVIN et al. is one such device. That is, the user must remove one tip having a set depth and replace it with another having a different set depth. This, of course, creates the problem of storing the replaceable tips, which if not properly done, may result in their misplacement, damage, contamination, or the like.

An improved device would allow the user to more easily adjust the depth of penetration and would overcome some of the disadvantages described above. Moreover, since the skin thickness can vary slightly from user to user and finger to finger, a need exists for efficiently adapting the depth of penetration. For example, an index finger may be more calloused than a middle finger, and the more calloused finger will typically have thicker skin. By adjusting the depth of puncture so that the depth is no greater than necessary for extracting a required amount of blood, any pain experienced by the user may be minimized.

Lancets having an adjustable tip are known per se. For example, U.S. Pat. No. 4,469,110 to SLAMA discloses a mechanism which adjusts the penetration depth by rotating a threaded sleeve relative to a body. The SLAMA device is characterized as a "single bottom" device which employs a threaded design which can be expensive to manufacture. Moreover, such a device may require the user to rotate the threaded sleeve up to 360 degrees and more in order to attain the proper depth setting. Further, such a threaded resign is prone to inadvertent setting changes since there is nothing but frictional engagement between the mating threads to maintain the adjustment setting.

U.S. Pat. No. 4,895,147 to BODICKY et al. functions in a similar manner to the device in SLAMA and therefore suffers from similar disadvantages.

U.S. Pat. Nos. 5,464,418, 5,797,942, 5,908,434, 6,156,051 and 6,530,937 to SCHRAGA also disclose similar lancet devices and are hereby incorporated herein by reference as though set forth in full herein.

As disclosed in U.S. Pat. No. 5,908,434, the lancet device has a body portion which encloses a lancet and a lancet firing mechanism. The lancet typically has a needle extending therefrom and is caused to move towards the tip of the device by a trigger or firing mechanism. The lancet device forces the needle, by virtue of the needle being fixed thereto, out of the device by some distance or depth so that the needle can penetrate the skin of the user. The function of this firing mechanism and the lancet body design is disclosed in each of 5,797,942 and 5,908,434. These Patents are incorporated by reference herein in their entirety and are therefore only briefly discussed herein.

What is needed is a lancet device which can accurately and precisely control the depth of penetration of the needle relative to the surface of the user's skin while also being easy to use. It is also desirable for the user to be able to use and adjust the depth penetrating setting with just one hand and/or with less effort that currently required with existing lancet devices.

Thus, while advances have been made, there is a continuing need for a lancet device which provides for convenient, reliable and easy adjustment of penetration depth.

SUMMARY OF THE INVENTION

According to one aspect of the invention there is provided a lancet device that includes a body. A trigger is preferably mounted to the body, although it can be operatively associated with the body in any other way. A front cover includes a skin engaging end that includes a lancet opening through which a lancet needle extends. A holding member is movably mounted within the body and comprises a front end and a rear end. The front end is configured to receive a lancet. A stop surface moves with the holding member. A cam wheel includes cam surfaces which can be contacted by the stop surface. The cam wheel is configured to rotate at least partially. The cam wheel rotates about an axis that is parallel to an axis running through at least one of the lancet opening and the holding member.

The lancet device may further comprise a back cap configured to move between a retracted position and an original position. The back cap may be configured to move the holding member to a retracted position. The back cap may be coupled to a surface that engages the rear end of the holding member. The back cap may be coupled to in inner sleeve that includes a surface that engages the rear end of the holding member. The inner sleeve may comprise an opening that receives a rear end of the holding member. The back cap may be coupled to an inner sleeve that includes a surface that engages projections disposed on the rear end of the holding member.

The lancet device may further comprise a spring for biasing the back cap towards an original position. The lancet device may further comprise a first spring for biasing the holding member towards an extended position and a second spring for biasing the holding member in an opposite direction. The first and second springs may be arranged within an axial opening of the holding member. The first spring may contact one side of a projection extending inwardly from the body and the second spring may contact another side of the projection. The projection may extend into an elongated slot formed in the holding member.

The lancet device may further comprise an end plug mounted to the rear end of the holding member. The first spring may be disposed between the projection and an inner wall surface arranged in the area of the front end of the holding member and the second spring may be disposed between the projection and the end plug. The trigger may be movably mounted to the body. The front cover may be removably mounted to the body. The holding member may comprise a projection that includes the stop surface. The holding member may comprise an integrally formed projection that includes the stop surface. The front end of the holding member may comprise an opening that is configured to removably receive the lancet.

The lancet device may further comprise a deflecting member configured to be deflected by the trigger. The deflecting member may be coupled to the holding member. The deflecting member may comprise a first stop surface or end that contacts a first surface of a holding projection extending inwardly from the body. The cam wheel may comprise indicia. The cam wheel may be a thumb wheel. The cam surfaces of the cam wheel may be arranged on a cam section of the cam wheel. The cam section may be disposed on an annular side of the cam disk while an outer circumferential surface of the cam wheel includes the indicia. The cam wheel may comprise a centrally disposed opening that is mounted about or around the holding member. The opening in the cam wheel may be large enough to allow the holding member to move within it. The opening may comprise a center axis that is generally the same as the axis running through the holding member. The cam wheel may rotate about an axis that is generally the same as an axis running through at least one of the lancet opening and the holding member. The cam wheel may be disposed between the trigger and a back cap. The body may comprise a two piece body. The cam wheel may be axially retained between inwardly projecting portions of the body. The cam wheel may be disposed between a main projection of the body and a back cap. The front cover may be removably mounted to the two piece body. The lancet device may further comprise a back cap movably mounted to the two piece body. The body may comprise at least one curved side indentation through which the cam wheel protrudes. The body may comprise two oppositely arranged curved side indentations. The body may comprise a mechanism for viewing indicia of the cam disk. The mechanism for viewing indicia of the cam disk may comprise an opening. The opening may be a generally rectangular slot. The lancet device may further comprise projecting walls for one of axially retaining the cam wheel, whereby the walls allow the cam wheel to rotate within the body while being axially retained therein.

The invention also provides a method of puncturing a surface of skin using the lancet device described above, wherein the method comprises adjusting a set depth of penetration of the needle by moving the cam wheel to a desired set position, disposing the skin engaging end of the lancet device against a user's skin, and triggering the trigger to cause the lancet needle to penetrate the user's skin, wherein the puncture allows a blood sample to be taken.

The invention also provides a method of using the lancet device described above, wherein the method comprises at least partially rotating the cam wheel to a desired set position, moving the holding member to a retracted position, maintaining the holding member in the retracted position until the trigger is triggered, disposing the skin engaging end of the lancet device against a user's skin, and triggering the trigger to cause movement of the holding member.

The invention also provides a lancet device, that includes a body, a trigger, a front cover comprising a skin engaging end that includes a lancet opening through which a lancet needle extends. A holding member is movably mounted within the body and comprising a front end a rear end. The front end is configured to receive a lancet. A stop projection is coupled to the holding member. A cam wheel comprises indicia and cam surfaces which can be contacted by the stop projection. The cam wheel is configured to rotate at least partially. The cam wheel is mounted to rotate about or around the holding member.

The invention also provides a lancet device comprising a body, a trigger, a front cover comprising a skin engaging end that includes a lancet opening through which a lancet needle extends. A holding member is movably mounted within the body and comprising a front end a rear end. The front end is configured to receive a lancet. A back cap is configured to move the holding member to a retracted position. A stop surface is coupled to the holding member. A cam wheel is at least partially arranged within the body. The cam wheel comprises indicia and cam surfaces which can be contacted by the stop projection. The cam wheel is configured to rotate at least partially on an axis that is parallel to an axis of the holding member. The cam wheel protrudes from at least one side wall of the body.

Other exemplary embodiments and advantages of the present invention may be ascertained by reviewing the present disclosure and the accompanying drawing.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein:

FIG. 6A shows a right side view of the embodiment shown in FIG. 1;

FIG. 6B shows a top view of the embodiment shown in FIG. 6A;

FIG. 6C shows a left side view of the embodiment shown in FIG. 6B;

FIG. 6D shows a front end view of the front cap of the embodiment shown in FIG. 6C;

FIG. 6E shows a front end view of the embodiment shown in FIG. 6B, except that the trigger is not shown;

FIG. 6F shows a rear end view of the embodiment shown in FIG. 6B;

FIG. 7A shows a cross-section view of the right body part of the lancet device shown in FIG. 1;

FIG. 7B shows an inside view of the right body part shown in FIG. 7A;

FIG. 7C shows an outside view of the right body part shown in FIG. 7A;

FIG. 7D shows a front cross-section view of the left-most sectioning arrows shown in FIG. 7B;

FIG. 7E shows a front end view of the right body part shown in FIG. 7C;

FIG. 7F shows a rear end view of the right body part shown in FIG. 7A;

FIG. 7G shows a rear cross-section view of the right-most sectioning arrows shown in FIG. 7B;

FIG. 7H shows a rear cross-section view of the middle sectioning arrows shown in FIG. 7B;

FIG. 8A shows an outside view of the left body part of the lancet device shown in FIG. 1;

FIG. 8B shows a cross-section view of the left body part shown in FIG. 8A;

FIG. 8C shows a bottom view of the left body part shown in FIG. 8B with inner surfaces shown in hidden lines;

FIG. 8D shows an inside view of the left body part shown in FIG. 8A;

FIG. 8E shows a front end view of the left body part shown in FIG. 8A;

FIG. 8F shows a front cross-section view of the left-most sectioning arrows shown in FIG. 8D;

FIG. 8G shows a rear end view of the left body part shown in FIG. 8B;

FIG. 8H shows a rear cross-section view of the right-most sectioning arrows shown in FIG. 8D;

FIG. 8I shows a rear cross-section view of the middle sectioning arrows shown in FIG. 8D;

FIG. 11A shows a rear view of the cam wheel of the lancet device shown in FIG. 1;

FIG. 11B shows a cross-section view of the cam wheel shown in FIG. 11A;

FIG. 11C shows a front view of the cam wheel shown in FIG. 11B;

FIG. 11D shows an outside view of the cam wheel shown in FIG. 11B;

FIG. 17A shows a front end view of the trigger element of the lancet device shown in FIG. 1;

FIG. 17B shows a top view of the trigger element shown in FIG. 17A;

FIG. 17C shows a rear view of the trigger element shown in FIG. 17B;

FIG. 17D shows a side view of the trigger element shown in FIG. 17B;

FIG. 17E shows a bottom view of the trigger element shown in FIG. 17B;

FIG. 17F shows a partial enlarged view of a front part of the trigger element shown in FIG. 17D;

FIG. 17G shows a partial enlarged view of the textured part of the trigger element shown in FIG. 17B;

FIG. 18A shows a top view of the back cover shown in FIG. 1;

FIG. 18B shows a rear view of the back cap shown in FIG. 18A;

FIG. 18C shows a side view of the back cap shown in FIG. 18A;

FIG. 18D shows a cross-section view of the back cap shown in FIG. 18A;

FIG. 18E shows a cross-section view of the back cap shown in FIG. 18C;

FIG. 19A shows a cross-section view of the inner sleeve member of the lancet device shown in FIG. 1;

FIG. 19B shows a rear view of the inner sleeve member shown in FIG. 19A; and

FIG. 19C shows a top cross-section view of the inner sleeve member shown in FIG. 19A.

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

Figure 1:
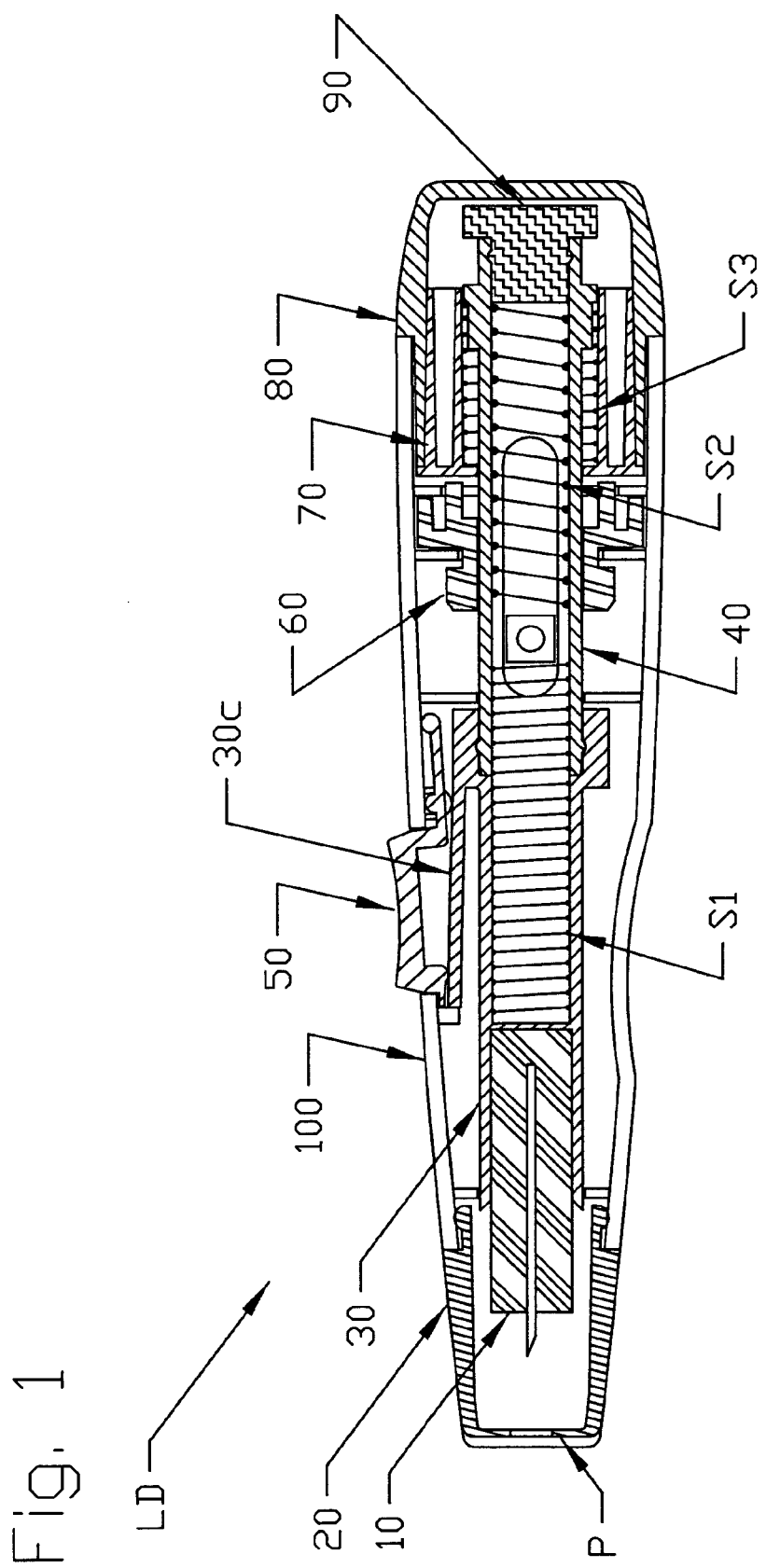
FIG. 1 shows a side cross-section view of one embodiment of the lancet device. The device is shown in the loaded (trigger set) position. The lancet is also shown in cross-section.

FIG. 1 shows a side cross-section view of one embodiment of lancet device (the lancet 10 is also shown in cross-section). Lancet device LD has a lancet body made up of a right side body portion 100 and a left side body portion 110 (see FIG. 4). These parts 100 and 110 are connected, e.g., using adhesives and/or fasteners and/or welding and/or snap-together holding mechanisms (not shown) to each other when the lancet device LD is initially assembled. A holding member 30/40 is movably disposed within the body parts 100, 110. Also, a front cover 20 is removably connected or attached to a front portion of the body parts 100, 110. By removing the front cover 20, one can gain access to the lancet 10. The lancet 10 can thus be removed and replaced with a new lancet 10, as needed, once the front cover 20 is removed. As in many prior art lancet devices, the lancet device defines a plane P which is configured to contact (i.e., be positioned against) a user's skin. However, unlike known lancet devices, the instant embodiment may utilize an inwardly curved surface plane P beyond which the lancet need can extend. Next, a back cap 80 is arranged at a rear portion of the body parts 100, 110. The back cap 80 has a rear portion that can be gripped by a user and a front portion that slides within the body parts 100, 110. An inner sleeve 70 is connected (after being slid into the back cap 80) to the back cap 80 upon assembly of the lancet device. As will be described in more detail later on, movement of the back cap 80 rearwardly (see FIG. 5), causes the holding member 30/40 to retract until it reaches the loaded position shown in FIG. 1. The lancet 10, itself, is conventional and includes a needle. It can be removed and replaced with a new one, as is the case in many prior art lancet devices. To ensure that lancet 10 is securely (yet removably) retained within the lancet device, the front portion 30 of the holding member 30/40 includes a lancet holding end which receives the lancet 10 therein.

As can be seen in FIG. 1, the holding member 30/40 arrangement preferably has three springs mounted thereto. In this regard, a first spring S1, which can be made of spring steel, is arranged within the holding member 30/40, just behind the lancet receiving portion. Preferably, the first spring S1 has a diameter of approximately 6.2 mm, a freelength of approximately 36.7 mm, and a wire size of 0.5 mm. This spring S1 causes (and/or biases) the holding member 30/40 to move towards an extended position once a trigger 50 is activated (see FIG. 2). The trigger 50 includes a portion that is arranged within the body parts 100/110, and is mounted to these body parts 100, 110. The trigger 50 also has a finger engaging (e.g. push button) portion 50a that can be pushed and/or deflected into the lancet device. The trigger 50 functions as a spring in that it is capable of deflecting inwards (see FIG. 2) when force is applied to the finger engaging portion 50a, and is also capable of returning to a pre-deflection position (see FIGS. 1 and 3). A second spring S2, which can be made of spring steel, is also arranged within the holding member 30/40 arrangement, but behind the first spring S1. Preferably, the second spring S2 has a diameter of approximately 6.2 mm, a freelength of approximately 25.5 mm, and a wire size of 0.5 mm. This spring S2 causes (and/or biases) the holding member 30/40 arrangement to move back towards a retracted position once the lancet 10 reaches the extended position. In this way, the lancet 10 (and holding member 30/40) is automatically retracted after puncturing the skin of a user. A third spring S3, which can also be made of spring steel, is externally mounted to a rear portion 40 of the holding member arrangement 30/40. Preferably, the third spring S3 has a diameter of approximately 10.1 mm, a freelength of approximately 13.6 mm, and a wire size of 0.25 mm. This spring S3 causes (and/or biases) the back cap 80 (and attached inner sleeve 70) to move inwardly within body parts 100, 110. When a user wishes to place the lancet device LD in the loaded position (see FIG. 1), a user need only move back cap 80 rearwardly (see FIG. 5) until the holding member arrangement 30/40 reaches the position shown in FIG. 1. This, in turn, compresses the third spring S3 to a certain extent. However, when the user releases the back cap 80, spring S3 causes the back cap 80 to return to the position shown in FIGS. 1–4.

The lancet device LD also utilizes a cam wheel 60 to adjust the penetration depth of the lancet needle. The cam wheel 60 is preferably mounted within both body parts 100, 110 so as to be at least partially rotatable in each of two directions. Of course, the cam wheel 60 can be mounted within the body in any desired manner provided it functions properly in the intended manner. To ensure that the cam wheel 60 is axially retained to body parts 100, 110, yet allowed to rotate with respect to the lancet device body, retaining walls 100h, 100i, 110h and 110i are utilized. These will be more fully described with regard to FIGS. 7 and 8. The cam wheel 60 also has a plurality of cam surfaces 60e1–60e8 (see FIG. 11E) which are configured to be engaged by a stop projection 40i (in particular stop surface 40i1 of stop projection 40i) that is formed on or coupled to the rear portion 40 of holding member 30/40. Finally, the lancet device LD also utilizes an end plug 90 that ensures that the spring S2 is retained within the holding member 30/40.

Figure 2:
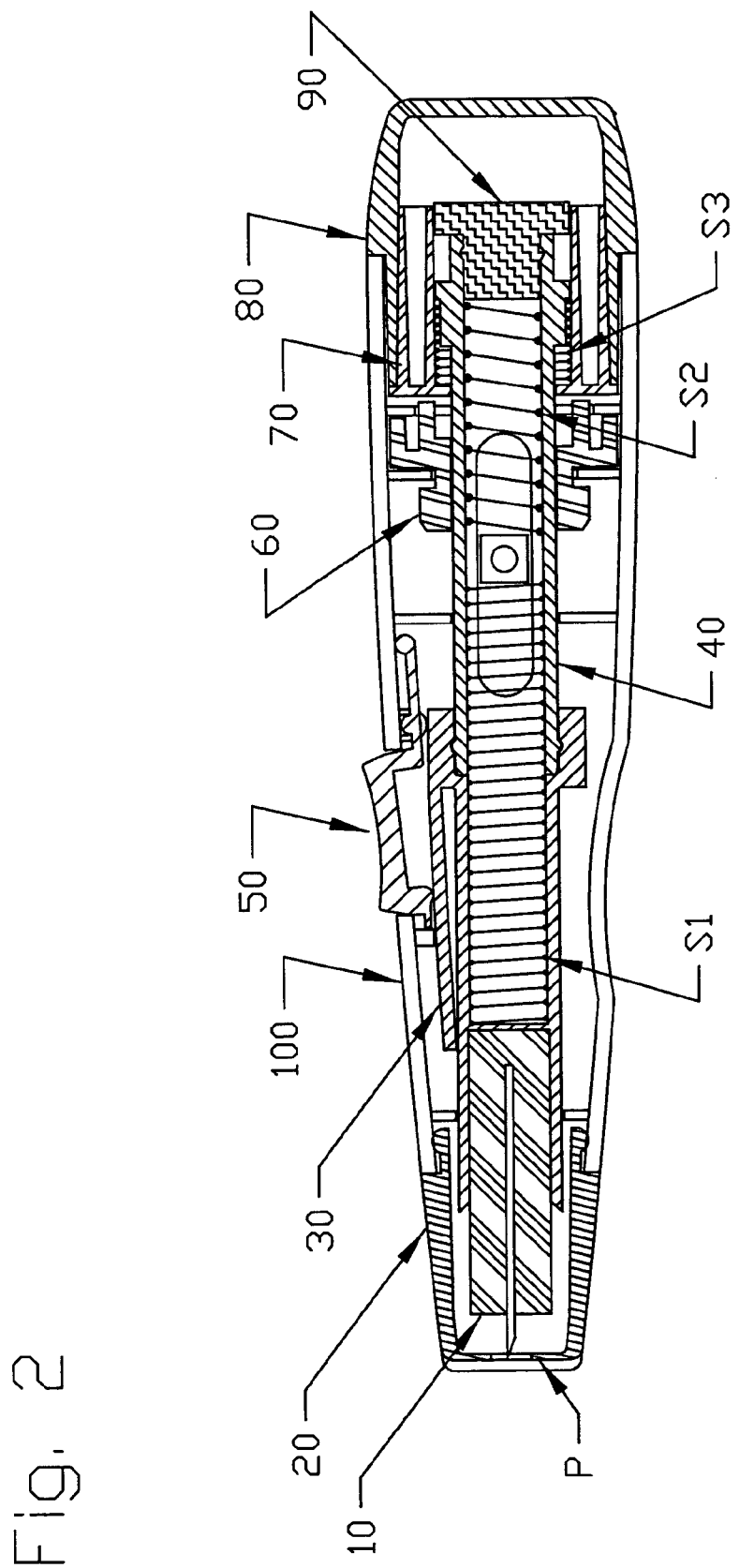
FIG. 2 shows a side cross-section view of the embodiment of FIG. 1. The device is shown with the lancet needle moving toward a pre-set depth position after it has been triggered.

As described above, FIG. 1 shows the lancet device LD with the lancet member 30/40 in the loaded position, i.e., ready to move to an extended position when the trigger 50 is pressed. The holding member 30/40 retains the loaded position of FIG. 1 as a result of engagement between a deflecting member 30c and shoulders that are formed by projections 100g and 110g of the body parts 100, 110. On the other hand, FIG. 2 shows what happens when the trigger 50 is pressed, i.e., the trigger 50 is caused to be deflected inwardly. That is, the holding member 30/40 is released from the loaded position of FIG. 1, and is caused to move towards plane P. This occurs because the trigger 50 causes the deflecting member 30c to disengage from the projections 100g/110g of the body parts 100/110. As discussed above, this movement is caused by the expansion (in the direction of the axis of the holding member 30/40) of first spring S1. The holding member 30/40 continues to move towards the plane P until the stop projection 40i contacts or engages one of the stop surfaces 60e1–60e8 of the cam wheel 60. Once the trigger 50 is released (once a user stops pressing on the trigger 50), the trigger 50 preferably moves back (e.g., automatically) to an un-deflected state shown in FIG. 3. The lancet device LD is then ready to be reloaded, i.e., it can then be placed back into the position shown in FIG. 1.

Figure 3:
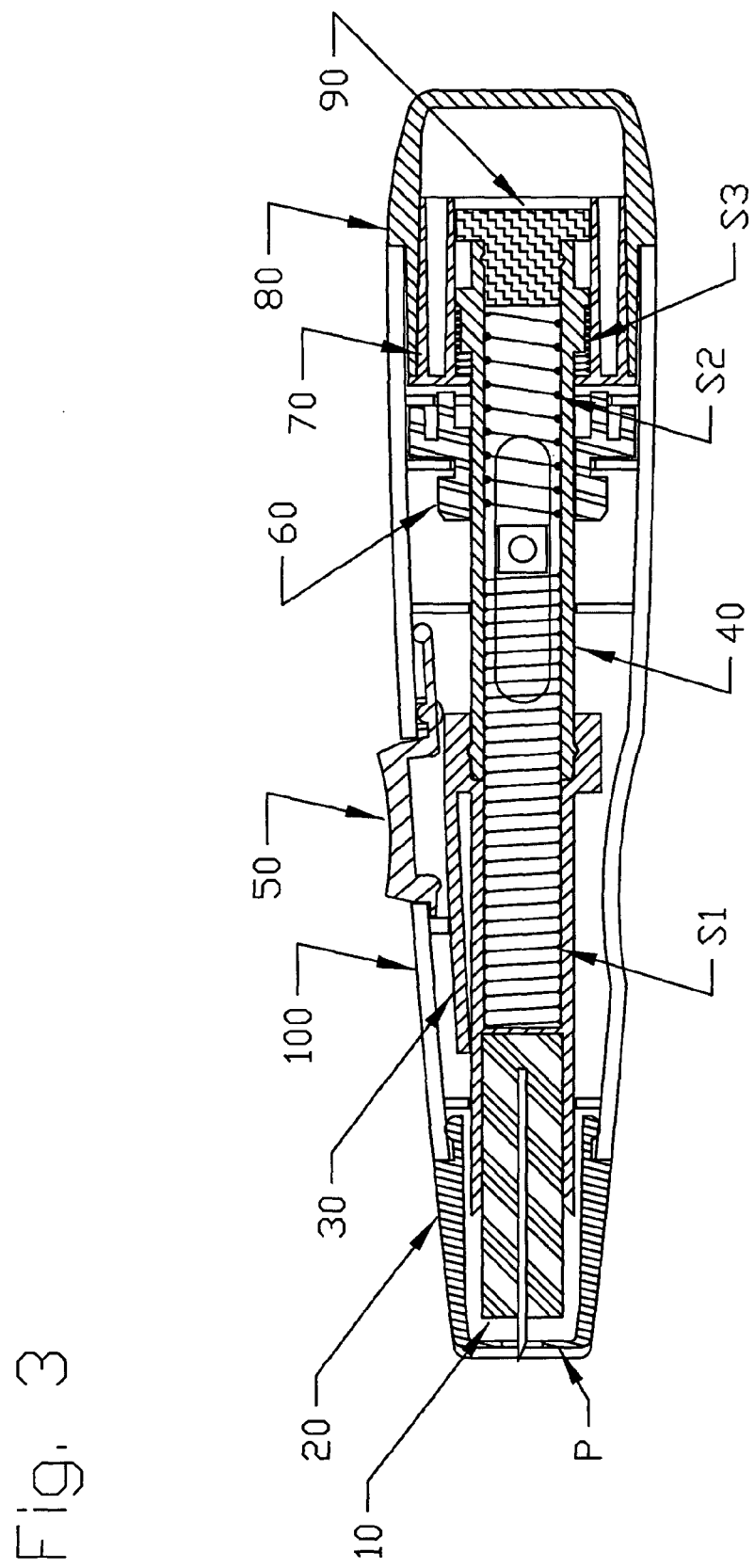
FIG. 3 shows a side cross-section view of the embodiment shown in FIG. 1. The device is shown with the lancet needle at a pre-set depth position.

FIG. 3 shows the lancet device LD with the holding member 30/40 in one of the pre-set extended positions, i.e., in one of the extended positions that will cause a desired puncture depth in the skin of a user (not shown). The distance that the lancet needle projects past plane P is thus determined by rotating the cam wheel 60 until the desired setting is reached. This setting, in turn, causes a particular stop surface (i.e., one of surfaces 60e1–60e8) to be placed in the path of the stop projection 40i. The various stop surfaces (e.g., 8 surfaces shown in FIG. 11E) of the cam wheel 60 thus determine how much the holding member 30/40 will move in the extended position relative to the plane P. The depth setting is thus controlled by contact between the stop projection 40i and one of the surfaces 60e1-60e8 of the cam wheel 60 (see FIG. 4). FIG. 3 also shows the needle tip projecting through the opening LO in the front cover 20 and past the plane P. And, as discussed above, the trigger 50 has returned to a non-deflected original position.

Figure 4:
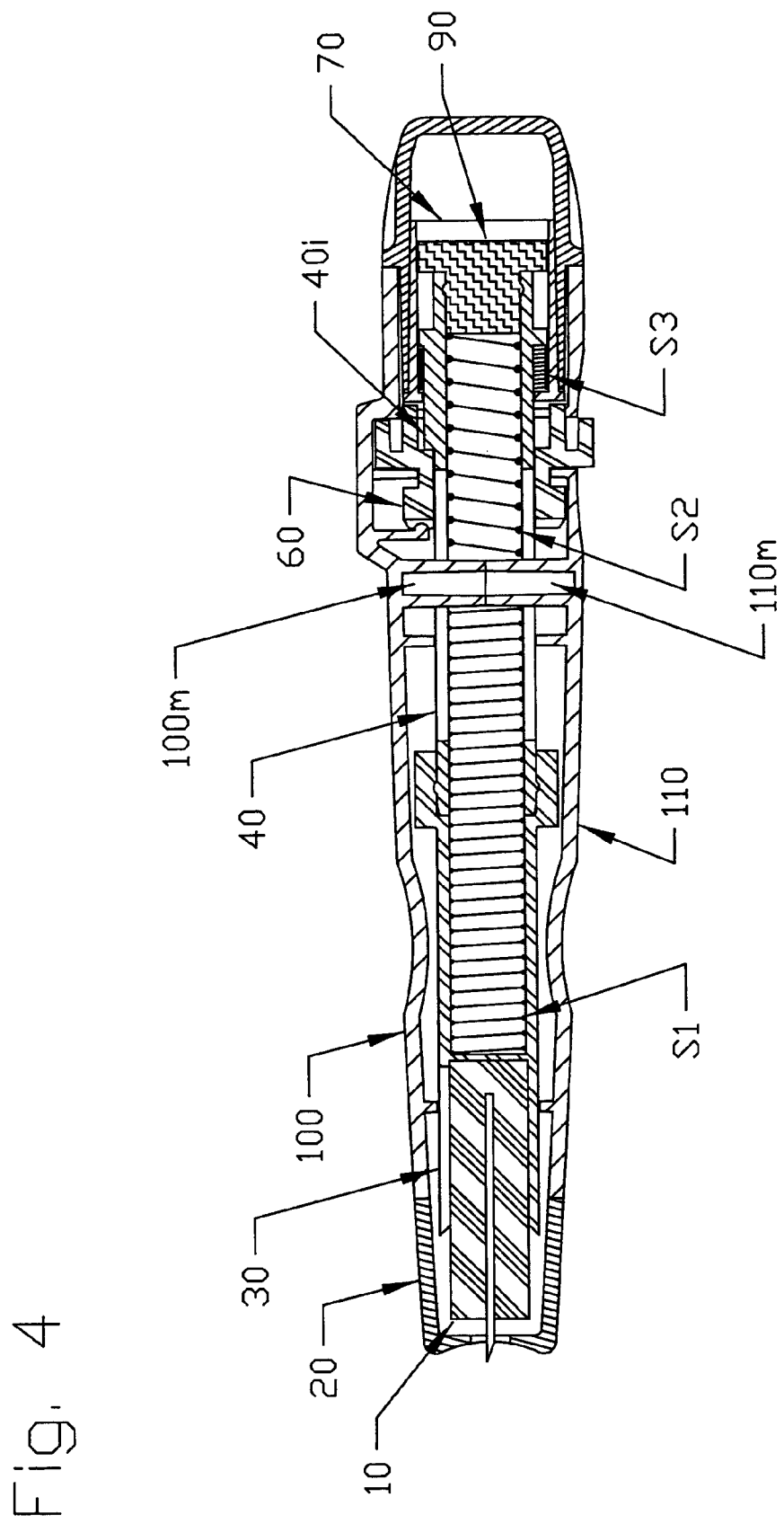
FIG. 4 shows a top cross-section view of the embodiment shown in FIG. 1 and in the position shown in FIG. 3.

FIG. 4 shows a top cross-section view of the lancet device of FIG. 1. In this regard, the holding member 30/40 is in the position shown in FIG. 3. As in FIGS. 1–3, the front cover 20, back cap 80, inner sleeve 70, end plug 90, holding member 30/40 and lancet 10 can be seen in their installed and/or assembled position. However, this FIGURE allows one to more clearly see that the first spring S1 is arranged within the holding member 30/40, just behind the lancet receiving portion. The first spring S1 is preferably sized to slide into internal openings 30*f* and 40*l* of the holding member 30/40. More particularly, the first spring S1 is preferably disposed inside the holding member 30/40 and between an inner wall 30*g* (just behind lancet 10) of the front part 30 of the holding member 30/40 and a projecting guide member 100*m*/110*m* of the right and left body parts 100, 110. That is, the first spring S1 is axially retained between a left side surface of projecting guide member 100*m*/110*m* and the inner wall 30*g* of the front portion 30 of the holding member 30/40. As a result, the first spring S1 is caused to be compressed when the holding member 30/40 is moved back (i.e., to the right) to a retracted position relative to the body parts 100, 110. The projecting guide member 100*m*/110*m* does not move because it is fixed to the body portions 100 and 110. Of course, the projecting guide member 100*m*/110*m* can be arranged and/or mounted within the body in any desired manner provided it functions for its intended purpose. It can even be formed only on one of the body parts 100, 110. As discussed above, the first spring S1 causes (and/or biases) the holding member 30/40 towards an extended position once a trigger 50 (not shown in FIG. 4) is activated. As a result, the holding member 30/40 cannot be moved back to a retracted position without causing the first spring S1 to be compressed thereby.

The second spring S2 is also preferably sized to slide into an internal opening 40*l* of the holding member 30/40. More particularly, the second spring S2 is disposed inside the holding member 30/40 and between an inner wall 90*b* of the end plug 90 and the projecting guide member 100*m*/110*m* of the body parts 100, 110. That is, the second spring S2 is axially retained between a right side surface of projecting guide member 100*m*/110*m* and the inner wall 90*b* of the end plug 90. The second spring S2 is caused to be compressed when the holding member 30/40 is moved forward (i.e., to the left) to an extended position relative to the body parts 100, 110. Again, the projecting guide member 100*m*/110*m* does not move because it is fixed to the body portions 100, 110. As discussed above, the second spring S2 causes (and/or biases) the holding member 30/40 towards a retracted position once the holding member 30/40 reaches the various pre-set extended positions (see e.g., FIG. 3). Thus, the second spring S2 is compressed when the holding member 30/40 is extended by the first spring S1. Spring S2 then expands axially to retract the holding member 30/40. In this way, the lancet needle only momentarily projects past the plane P in the extended position before it is caused to retract back in the lancet device by the second spring S2. As a result, the lancet needle only projects past or beyond the plane P for a very brief time (i.e., a fraction of a second when the trigger 50 is pressed) and is otherwise not exposed to a user while the front cover 20 is installed thereon. Accordingly, a user or other innocent bystanders can be protected from being injured unintentionally by an exposed needle.

The third spring S3 is preferably sized to slide over a rear end of the rear portion 40 of the holding member 30/40. More particularly, the third spring S3 is disposed over a rear end of the rear portion 40 and between an inner wall 70*d* of the inner sleeve 70 and an annular shoulder 40*e* of the rear portion 40. That is, the third spring S3 is axially retained between a left side inner surface 70*d* of the inner sleeve 70 and the annular shoulder 40*e*. As a result, the third spring S3 is caused to be compressed when the back cap 80 is moved rearward (i.e., to the right as in FIG. 5) to an extended position relative to the body parts 100, 110. As discussed above, the third spring S3 causes (and/or biases) the back cap 80 towards a retracted position (i.e., sliding back into the lancet device) once a user releases the back cap 80 (compare FIG. 5 to FIG. 1). Thus, the third spring S3 is compressed when the back cap 80 is pulled backwards (to the right in FIG. 5) to cause the deflecting member 30*c* to seat onto the projections 100*g*/110*g* (adjacent the trigger 50) of the body parts 100, 110. The third spring S3 then expands axially to cause the back cap 80 to move to the left until shoulders 80*c* of the back cap 80 contact end edges 100*b*, 110*b* of the body parts 100, 110. However, the spring S3 does not compress completely when the back cap 80 is extended (moved to the right). This is because the left side inner surface 70*d* of inner sleeve 70 contacts surfaces 40*j*1 and 40*k*1 two oppositely arranged projections 40*j* and 40*k* of the rear portion 40 of the holding member 30/40.

Figure 5:
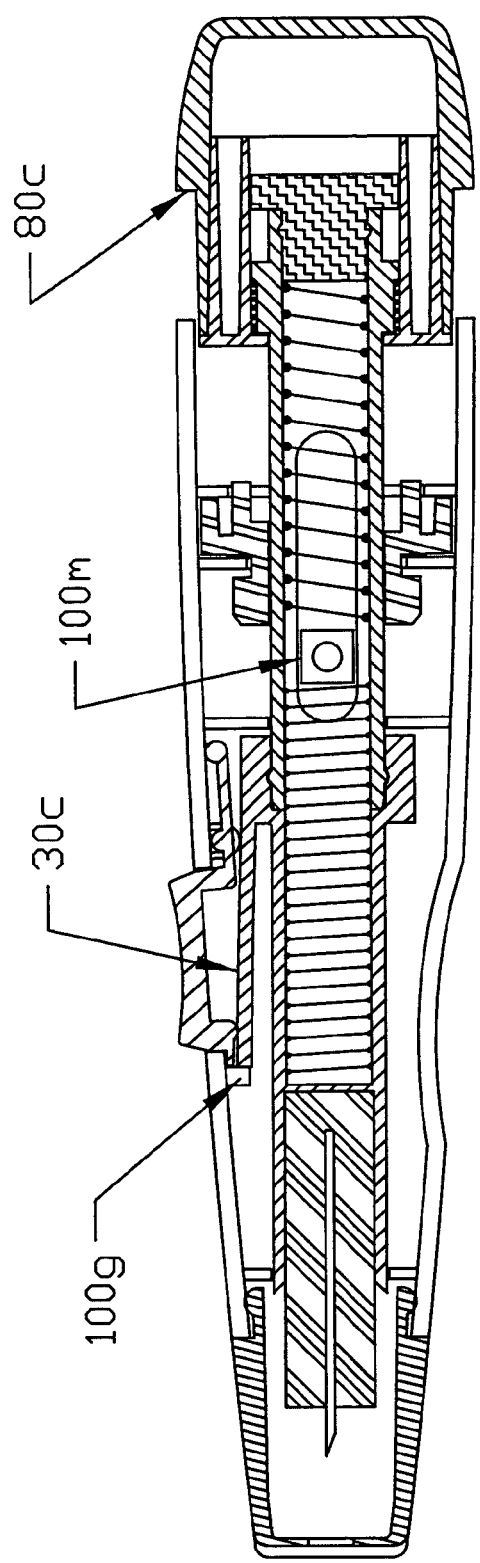
FIG. 5 shows a side cross-section view of the embodiment shown in FIG. 1. The device is shown in the loaded (trigger set) position after it has been so positioned by retracting the trigger setting mechanism.
Figure 9A:
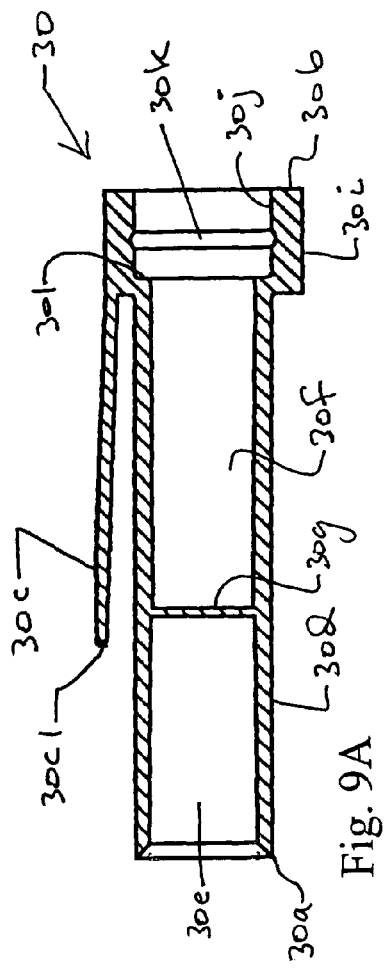
FIG. 9A shows a side cross-section view of the front portion of the holding member used in the lancet device shown in FIG. 1.
Figure 9B:
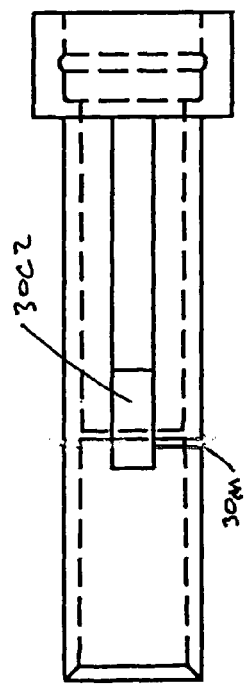
FIG. 9B shows a top view of the front portion shown in FIG. 9A.
Figure 9C:
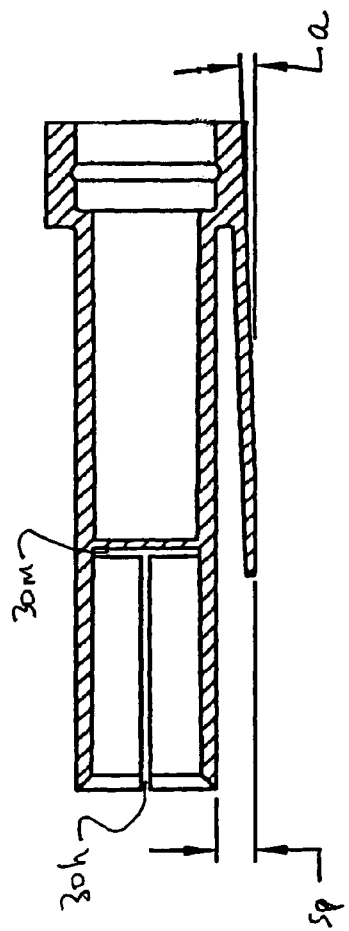
FIG. 9C shows another side cross-section view of the front portion shown in FIG. 9A.
Figure 9D:
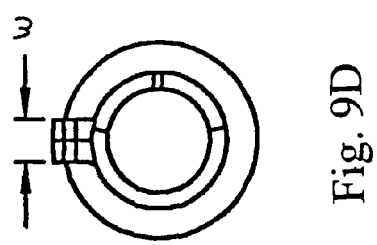
FIG. 9D shows a front end view of the front portion shown in FIG. 9A.

FIG. 5 shows another cross-section side view of the lancet device LD shown in FIG. 1. In FIG. 5, the back cap 80 is shown in the extended position. As described above, this movement is used to retract the holding member 30/40 until the deflecting member 30*c* engages the projections 100*g*/110*g* of the body parts 100, 110. At this point, the user need only release the back cap 80 so that the third spring S3 will automatically cause the back cap 80 to move or retract towards the lancet device until it assumes the position shown in FIG. 1. As can be seen when comparing FIGS. 2 and 5, the first spring S1 becomes compressed axially when the back cap 80 causes the holding member 30/40 to move to a retracted position (to the right). As a result, the second spring S2 expands axially (compare FIGS. 2 and 5), while the third spring S3 compresses axially (see FIG. 5). However, once the back cap 80 is released, the third spring S3 expands axially—which causes the back cap 80 (and the attached inner sleeve 70) to retract back into the lancet device (see FIG. 1).

FIGS. 6A–F show right side, top, left, front and rear views of the lancet device LD shown in FIGS. 1–5. As discussed above, the lancet device has a lancet body made up of a right body portion 100 and a left body portion 110. These parts 100 and 110 are connected to each other when the lancet device is initially assembled. In this regard, a seam line SL is preferably formed and/or provided between the edges 100*a*/110*a* and 100*b*/110*b* of the body parts 100, 110. The front cover 20 is preferably removably connected or attached to a front portion of the body parts 100, 110. As is shown in FIGS. 6B and 6E, the curved surface plane P has a lancet opening LO through which the lancet needle passes. The back cap 80 is arranged at a rear portion of the body parts 100, 110. The back cap 80 preferably has a rear portion with textured portions 80*q* and 80*n* (i.e., on each side of the back cap 80). These textured portions allow a user to more easily grip the back cap 80. As discussed above, movement of back cap 80 rearwardly (as in FIG. 5) causes the holding member 30/40 to retract until it reaches the loaded position shown in FIG. 1.

Again, with reference to FIGS. 6A–F, the trigger 50 preferably has a tear-drop shaped button 50*a* which can be pressed by a user to cause the lancet 10 to move to the extended position. The cam wheel 60 can be seen to project partially from a recessed portion 110n of the left body part 110. In this regard, the recess 110n preferably has an inwardly curved surface whose radius is greater than a radius of the cam wheel 60. In order to allow the user to see which cam surface (one of surfaces 60e1–60e8) is arranged in the path of the stop projection 40i (i.e., to adjust the desired depth setting) the left body part 110 has a window W (e.g., a through opening or slot 110p) through which one can read the indicia (e.g., numbers or other desired indicia such as letters or marks) of the cam wheel 60. As should be evident, the lancet device LD is configured with curved surfaces 100q, 110q and an ergonomic shape to enable a user to grip the device more securely, while also being able to rotate the cam wheel 60 with one or more fingers of the same hand. Unlike the devices of the prior art, one can adjust the depth of penetration without using both hands. Of course, some users may require two hands to place the lancet device in the loaded position, since they may not be able to pull the back cap 80 backwards without using both hands.

To ensure that there is a smooth transition between the various parts of the lancet device, certain edges are preferably made to have a curved and/or profiled arrangement. Thus, the front cover 20 has circular or curved upper and lower edges 20b (see also FIG. 16) and complex profile side edges 20a. Similarly, the right and left body parts 100, 110 have top, side and bottom edges which are shaped to correspond to the circular or curved upper side and lower edges of the front cover 20. The back cap 80 has straight upper, lower and side shoulder edges 80c (see also FIG. 18). Similarly, the right and left body parts 100, 110 preferably have rear top, bottom and side straight edges 100b/110b which are shaped to correspond to the straight shoulder edges 80c of the back cap 80. Additionally, the external surfaces of both the back cap 80 and the front cover 20 have a shape, arrangement and/or configuration which continues the curved and/or tapered external surfaces of the right and left body parts 100, 110.

FIGS. 7A–H show various views of the right body part 100. The right body part 100 can preferably be made as one-piece structure by e.g., injection molding. In this regard, it is preferably made of a plastic or synthetic resin such as, e.g., ABS plastic. The body part 100 may also be made of ABS—Metallic Silver and have a finish designated as SPI-A2. Additionally, the body part 100 may have an overall length that is approximately 3.04" (i.e., between edges 100a and 100b). This will ensure that the assembled lancet device can have an overall length of approximately 4.1". Of course, other materials and/or finishes may be utilized, without leaving the scope of the invention. Moreover, the body part 100 may even be made of a plurality of sections of parts which are joined together to form the complete body part 100, without leaving the scope of the invention.

The right body part 100 preferably has a curved front edge 100a and curved sides 100a1. The radius of this edge 100a may be approximately 0.38". As will be described later on with regard to FIG. 16, the front edge 100a is configured to abut curved edges 20a. Moreover, curved side edges 100a1 of body part 100 similarly abuts curved edges 20b of front cap 20. Recesses or indentations 100a2 are disposed between front edge 100a and a projecting shoulder or wall 100a3. The recesses 100a2 are arranged or configured to receive within it or otherwise engage with a projection 20c (see FIG. 16C) of front cap 20. In this regard, the projections 20c similarly have rounded portions that corresponds to the rounded bottom of recesses 100a2. Of course, the recess 100a2 may be continuous, or it need not extend continuous from side 100c to side 100d. It can instead be formed as intermitted recesses or it may have the form of a single short recess that is arranged only on inner surfaces of sides 100c and 100d. Alternatively, the body part 100 can have the projection while the front cap 20 has the recess. Of course, other connecting mechanisms, whether conventional or otherwise, may also be utilized in place of the projection and recess connection.

The body part 100 also has a curved upper surface US. This surface US extends from front edge 100a to rear edge 100b, and may have a radius of approximately 30" (or may be essentially straight). Arranged within the curved side 100c is a tear-drop shaped through opening 100f (note that the full opening is defined by partial opening 100f and partial opening 110f when the two body parts are connected). This partial opening 100f is sized and configured to receive the push button portion 50a of the trigger 50 (see FIG. 17). Of course, the opening 100f can have any desired size, shape or configuration provided it allows a user access to the trigger 50 and/or provided that it generally corresponds to the size, shape and configuration of the trigger 50. The opening 100f is formed in the upper wall 100c near an inwardly projecting shoulder 100g. As was described previously, this shoulder 100g is sized, shaped and/or configured to be engaged by the deflecting member 30c (see FIG. 9). In this regard, the projection 100g has a straight contact surface that is generally parallel to edge 100b and a bottom surface or edge that can range from being generally perpendicular to edge 100b, to being tapered or angled by as much as 15 degrees or more. As will be described later on with regard to FIG. 9, the straight contact surface of projection shoulder 100g is configured to be engaged by surface 30c1 of deflecting member 30c.

The upper body part 100 additionally preferably includes two plate-like projections or walls 100h and 100i which connect sides 100c and 100d to side 100e. The purpose of these projections 100h and 100i is to axially retain cam wheel 60. These projections 100h and 100i have inwardly curved edges 100h1 and 100i1. In this regard, the projections 100h and 100i are spaced apart by a distance that is slightly greater than a width "w1"of cam wheel 60 (see FIG. 11B). By ensuring that the projections 100h and 100i are spaced apart by an amount that is greater than a width "w1" of the cam wheel 60, the cam wheel 60 will be allowed to rotate with ease. In this regard, the width "w1" between inner surfaces of projections 100h and 100i should be slightly greater than approximately 0.16" to accommodate width w1 of cam wheel 60 being approximately 0.16". A C-shaped projection 100j (similar to projection 110j of FIG. 8D) also extends inwardly from the wall 100c (similar to wall 110c) of the body part 100 (similar to body part 110). The projection 100j forms a right half portion of a bearing system for the trigger 50. Together with the projection 110j (see FIG. 8), the parts 100j and 110j form two circular bearing supports for the trigger 50. As will be described later on with regard to FIG. 17, the journal elements 50c of the trigger 50 are mounted to the bearing supports 100j/110j. The body part 100 also preferably includes a connecting rib 100k that provides strength to the body part 100 and serves to guide holding member 30/40. In order to allow the holding member 30/40 move freely within the lancet device and without being obstructed by the rib 100k, a circular or curved recess 100k1 (see FIG. 7D) is formed in the center of the rib 100k. This recess 100k1 of the rib 100k can have a radius of approximately 0.17".

The right body part 100 further preferably includes a curved indentation 100l disposed on side 100d. The radius of indentation 100l can be approximately 1.76". A main projection 100m extends inwardly from body portion 100. The projection 100m has an internal opening and polygonal outer shape (i.e., square). The purpose of this projection is to guide the holding member 30/40 and to prevent it from rotating when it moves axially. It this regard, the projection 100m (together with projection 110m) is sized to fit within slot 40f of the rear portion of holding member 30/40. A pawl member 100p extends inwardly from body part 100. The pawl member 100p has a rounded projecting portion that engages a ratchet surface, i.e., undulating surfaces 60b1 (notches) and 60b2 (projections), of the cam wheel 60. The pawl 100p deflects towards and away from cam wheel 60 as the cam wheel 60 rotates. In this way, the cam wheel 60 is locked and/or temporarily retained at a desired set-depth position. The interaction between pawl 100p and cam wheel 60 can produce a sound such as, e.g., clicking, when the cam wheel 60 is rotated. In order to accommodate the cam wheel 60, the body part 100 includes an outward projecting portion 100n. The body part 100 also includes an inwardly curved finger engaging section 100q which may have a radius of approximately 0.82°.

As seen in FIG. 7C, the sides 100c and 100d can be planar or slightly curved outwardly (i.e., convex). The sides 100c and 100d can also preferably be curved or tapered outwardly in the width direction (i.e., see FIGS. 7G and H) and may be angled at an angle "a" of approximately 7 degrees (see FIG. 7F). The corners 100s where the side walls 100c and 100d meet wall 100e can be rounded and have a radius of approximately 0.1". The rear edge 100b of the body part 100 is a continuous straight edge that is configured to make contact with shoulder 80c of back cap 80 (see FIG. 18).

FIGS. 8A–I show various views of the left body part 110. The body part 110 can preferably be made as one-piece structure by e.g., injection molding. In this regard, it is preferably made of a plastic or synthetic resin such as, e.g., ABS plastic. The body part 110 may also have be made of ABS—Metallic Silver and have a finish designated as SPI-A2. Additionally, the body part 110 may have an overall length that is approximately 3.04" (i.e., between edges 110a and 110b). This will ensure that the assembled lancet device can have an overall length of approximately 4.1". Of course, other materials and/or finishes may be utilized, without leaving the scope of the invention. Moreover, the body part 110 may even be made of a plurality of sections of parts which are joined together to form the complete body part 110, without leaving the scope of the invention.

The body part 110 preferably has a front curved edge 110a and includes circular and/or curved side edges 110a1. The radius of curved edge 110a may be approximately 0.38". As will be described later on with regard to FIG. 16, the front edge 110a is configured to abut a curved edge 20a of front cap 20 until contact occurs between circular and/or curved edge 20a and edge 110a. A recess 110a2 is disposed between front edge 110a and connecting wall 110a3. This recess 110a2 is arranged on each of sides 110c, 110d, and possibly on side 110e. Moreover, they have a rounded bottom that is configured to receive or otherwise engage projections 20c (see FIG. 16C). In this regard, the projections 20c similarly has a rounded edge that generally corresponds to the rounded bottom of recesses 110a2. Of course, the recess 110a2 can be either a partial recess or a continuous one, i.e., it can extend continuously from side 110c to side 110d. Alternatively, it can instead be formed as intermitted recesses or it may have the form of a single short recess that is centrally arranged with respect to walls 110c and 100c and walls 100d and 110d (when the body parts 100 and 110 are assembled together). As another alternative, the body part 110 can have the projection while the front cap 20 has the recess. Of course, other connecting mechanisms, whether conventional or otherwise, may also be utilized in place of the projection and recess connection.

The body part 110 also preferably has a curved lower surface LS. An inwardly curved surface 110l is also provided which may have a radius of approximately 1.76". The lower body part 110 additionally preferably includes two plate-like projections or walls 110h and 110i which are generally arranged to connect sides 110c and 110d. The purpose of these projections 110h and 110i is to axially retain the cam wheel 60 in the same way described above with regard to walls 100h and 100i. In this regard, the projections 110h and 110i are spaced apart a distance similar to projections 100h and 100i described with respect to FIG. 7. These projections 110h and 110i also similarly have inwardly curved recesses of different sizes which allow portions of the cam wheel 60 to axially project therethrough (see e.g., FIG. 1). As can be seen in FIG. 1, walls 100h and 110h are generally aligned with one another and have inwardly curved recesses that serve as a bearing for surface 60c. Similarly, walls 100i and 110i are generally aligned with one another and have inwardly curved recesses that serve as a bearing for surface 60i. A C-shaped projection 110j extends from wall 110c of the body part 110 in the same way as projection 100j of body part 100 (but oppositely arranged therefrom). This projection 110j forms the other half of a bearing system for the trigger 50. Together with the projection 100j (see FIG. 7), i.e., right half of the bearing system, the parts 100j and 110j form two circular bearing supports for the trigger 50. As will be described later on with regard to FIG. 17, the journal elements 50c of the trigger 50 are mounted to or within the bearing supports formed by parts 100j/110j. The body part 110 additionally includes connecting ribs 110a3 and 110k that provides strength to the body part 110 and act to axially guide the holding member 30/40. In order to allow the holding member 30 move freely within the lancet device LD and without being obstructed by the ribs 110a3 and 110k, circular or curved recesses (see FIGS. 8D, 8E and 8G) are formed in the center of the ribs 110a3 and 110k. These recesses of the ribs 110a3 and 110k can have a radius of approximately 0.17".

The body part 110 further preferably includes a polygonal or square shaped main projection 110m that is generally centrally disposed relative to sides 110c and 110d. The purpose of this projection 110m is to axially and/or non-rotatably guide the holding member 30/40 within the lancet device and to serve as stop surfaces for springs S1 and S2 (see e.g., FIG. 1). The projection 110m has a polygonal (i.e., four sided or square) shaped outer surface. A left side surface of the projection 110m serves a contact or engage right end of spring S1 (see e.g., FIG. 1). A right side surface of the projection 110m serves a contact or engage left end of spring S2 (see e.g., FIG. 1). The projection 110m also has an inner recess or blind opening. This opening is mainly for ease of manufacture and to reduce material costs. As can be seen from FIG. 4, the length of the projection 110m is sized to abut projection 100m of body part 100 when body parts 100 and 110 are assembled together. Of course, there may be some clearance between projections 100m and 110m when the body parts 100 and 110 are assembled together. However, each projection 100m and 110m should be of sufficient length so as to project at least partially into the slot 40f of the back portion 40 of holding member 30/40.

The body part 110 also preferably includes circular or curved indented side portions 110q and 110n. Recess 110q may have a radius of approximately 0.82". Recess 110n may have a radius that is greater than approximately 1". As described previously, recessed portion 110n allows a user to access the cam wheel 60. That way, the user can use a finger to rotate the cam wheel 60 from side 110e. As seen in FIG. 8I, the sides 110c and 110d can be angled with an angle "a" of approximately 7 degrees. The sides 110c and 110d can also have outer surfaces US and LS which are curved outwardly in the length direction (i.e., see FIG. 8A) and have a radius of approximately 30" and 55" respectively. The corners 110s where the side walls 110c and 110d meet wall 110e can be rounded and have a radius of approximately 0.1". The rear edge 110b of the body part 110 is preferably a continuous straight edge that is configured to make contact with shoulder 80c of back cap 80 (see FIG. 18).

As discussed above, surface 110c extends from front edge 110a to rear edge 110b, and may have a radius of approximately 30". Alternatively, it may be essentially straight. Arranged within the curved side 110c is a tear-drop shaped through opening 110f (note that the full opening is defined by partial opening 100f and partial opening 110f when the two body parts are connected). This opening 110f is sized and configured to receive the push button portion 50a of the trigger 50 (see FIG. 17). Of course, the opening 110f can have any desired size, shape or configuration provided it allows a user access to the trigger 50 and provided that it generally corresponds to the size, shape and configuration of the trigger 50. The opening 110f is formed in the upper wall 110c near an inwardly projecting shoulder 110g. As was described previously, this shoulder 110g (as with shoulder 100g) is sized, shaped and/or configured to be engaged by the deflecting member 30c (see FIG. 9). In this regard, the projection 110g has a straight contact surface that is generally parallel to edge 110b and a bottom surface or edge that can range from being generally perpendicular to edge 110b to being tapered or angled by as much as 15 degrees or more. As will be described later on with regard to FIG. 9, the straight contact surface of projection shoulder 110g is configured to be engaged by surface 30c1 of deflecting member 30c.

FIGS. 9A–D show various views of the front portion 30 of the two-piece holding member 30/40. The front portion 30 can preferably be made as one-piece structure by e.g., injection molding. In this regard, it is preferably made of a plastic or synthetic resin such as, e.g., Delrin plastic. The front portion 30 may also be made of Delrin—Natural and have a finish designated as SPI-C1. Additionally, the front portion 30 may have an overall length that is approximately 1.6" (i.e., between edges 30a and 30b). Of course, other materials and/or finishes may be utilized, without leaving the scope of the invention. Moreover, the front portion 30 may even be made of a plurality of sections of parts which are joined together to form the complete front portion 30, without leaving the scope of the invention.

Front portion 30 preferably has a front end 30a and a cylindrical section 30d which may have a diameter of approximately 0.32". A front opening 30e is arranged within the cylindrical section 30d. The opening 30e extends from a wall 30g to edge 30a. The diameter "d" of the opening 30e at the edge 30a may be approximately 0.26" and may taper slightly inwards, e.g., by approximately 0.25 degrees (per side), i.e., towards wall 30g. This tapered opening 30e is sized and configured to securely and/or snugly retain and receive the lancet 10 (see e.g., FIG. 1) which may be a conventional lancet. Axial slot 30h and circumferential slot 30m allow walls of the opening 30e to expand and contract with removal and replacement of the lancet 10. The front portion 30 of holding member 30/40 also includes another cylindrical section 30i which may have a diameter of approximately 0.46". Another internal opening 30f extends from shoulder 30l to a wall 30g. The opening 30f is sized and configured to receive spring S1 (see e.g., FIG. 1). The internal diameter of the opening 30f at the shoulder 30l may be approximately 0.24" and may taper slightly, e.g., by approximately 0.25 degrees (per side), towards wall 30g. Cylindrical section 30i also has an internal opening 30j that extends from edge 30b to shoulder 30l. The opening 30j is sized and configured to receive end 40a of rear portion 40 of holding member 30/40 (see e.g., FIG. 1).

A deflecting member 30c preferably extends from cylindrical section 30i. This deflecting member 30c has a stop surface 30c1 which is configured to abut shoulders 100a3 and 110a3 of the body parts 100 and 110. An upper surface 30c2 of the deflecting member 30c, near end 30c1, is designed to be engaged by the trigger 50 (see FIG. 1). Specifically, this surface 30c2 is configured to be engaged by projection 50e of the trigger 50. As explained above, the deflecting member 30c is capable of deflecting inwards towards the front portion 30 when it is forced inwards towards holding member 30/40. However, because the deflecting member 30c acts like a natural spring, the deflecting member 30c is capable of deflecting away from the front portion 30 when it is not being forced towards holding member 30/40. In this regard, the deflecting member 30c is formed with an angle "a" of approximately 2 degrees relative to cylindrical surface 30i. The end 30c1 of the deflecting member 30c can be spaced from surface 30d by approximately 0.09". In the area 30c2 where the deflecting member 30c is engaged by the projection 50e of the trigger 50, the outer surface may be parallel to cylindrical surface 30d. Thus, the distance "sp" can be about 0.09". The deflecting member 30c also has a width "w" (measured in the direction of FIG. 9D) of approximately 0.1".

Inner diameter 30j of front portion 30 also preferably includes a continuous rounded recess 30k which is sized and shaped to receive the continuous rounded projection 40c of the rear portion 40. In this way, the two parts 30 and 40 can be coupled and/or assembled together. Of course, the projection can be formed on the part 30 and the recess formed on part 40 without leaving the scope of the invention. Moreover, the recess and projection need not be made continuous and can instead be intermittently formed. The invention also contemplates other connecting mechanisms besides a projection/recess connection such as, e.g., an adhesive attachment.

Figure 10A:
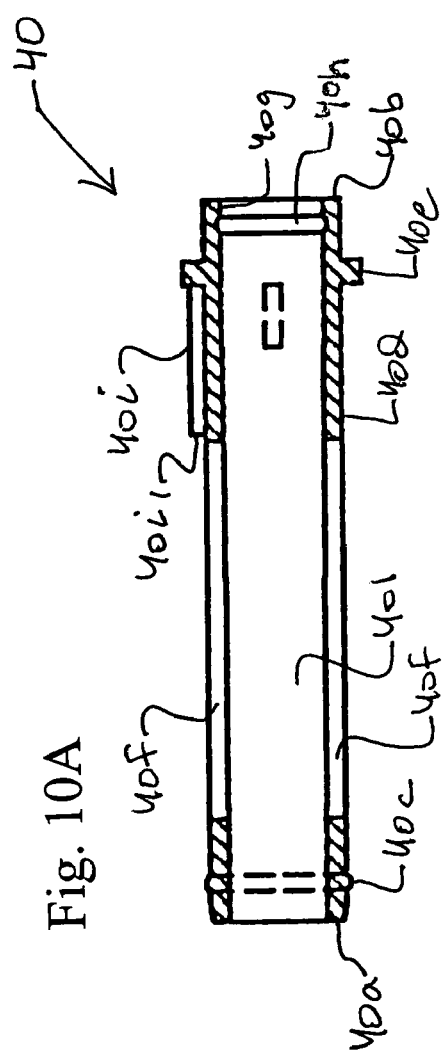
FIG. 10A shows a side cross-section view of the rear portion of the holding member used in the lancet device shown in FIG. 1.
Figure 10B:
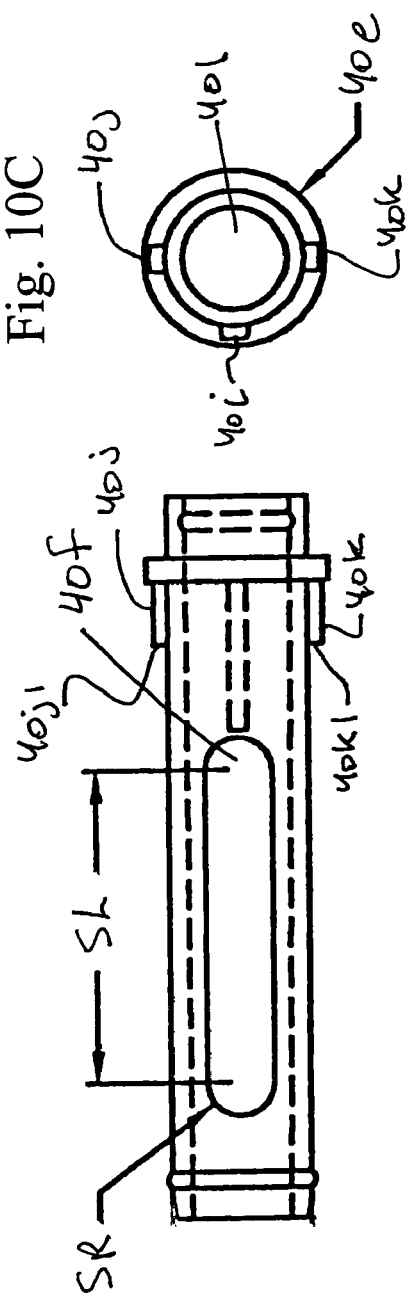
FIG. 10B shows a bottom view of the rear portion shown in FIG. 10A.
Figure 10C:
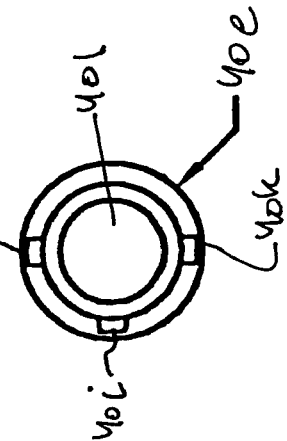
FIG. 10C shows a front end view of the rear portion shown in FIG. 10B.

FIGS. 10A–C show the rear portion 40 of the two-piece holding member 30/40. The length between end 40a and end 40b can be approximately 1.72". As discussed above, front end of rear portion 40 has a projection 40c which engages recess 30k of the front portion 30. A cylindrical section 40d extends from projection 40c to circumferential shoulder 40e. The cylindrical section 40d may have a diameter of approximately 0.32". Between the projection 40c and end 40a, the outer surface may taper or curve inwards to facilitate entry of end 40a into opening 30j. A through opening 40l is arranged within the cylindrical section 40d. The opening 40l extends from end 40a to end 40b. The diameter of the opening 40l may be approximately 0.24" and, at the edge 40b, may be approximately 0.244" and may taper slightly, e.g., by approximately 0.25 degrees (per side), towards end 40a. This tapered opening section 40g is sized and configured to securely retain and receive the plug 90 (see e.g., FIG. 1). The opening 40l is sized and configured to receive springs S1 and S2 (see e.g., FIG. 1). A recess 40h is arranged within opening 40g and is designed to receive projection 90d of plug 90 (see FIG. 12). The rounded recess 40*h* may be continuous and may be sized and shaped to receive the continuous rounded projection 90*d* of the plug 90. In this way, the parts 40 and 90 can be coupled and/or assembled together. Of course, the projection can be formed on the part 40 and the recess formed on part 90 without leaving the scope of the invention. Moreover, the recess and projection need not be made continuous and can instead be intermittently formed. The invention also contemplates other connecting mechanisms besides a projection/recess connection such as, e.g., an adhesive attachment.

End 40*b* of the rear part 40 also preferably includes three projections 40*l*, 40*j* and 40*k*. Short projections 40*j* and 40*k* extend in the direction of the axis of the rear portion 40 and are arranged opposite one another, i.e., 180 degrees apart. These projections 40*j* and 40*k* may have a length of approximately 0.21" and a width of approximately 0.05". Short projections 40*j* and 40*k* also have stop surfaces 40*j*1 and 40*k*1. These surfaces 40*j*1 and 40*k*1 are adapted to be engaged and/or contacted by surface 70*d* of the inner sleeve 70 when the back cap 80 is moved backwards to load the lancet device (see FIG. 5). Longer projection 40*i* includes a stop shoulder or surface 40*i*1. As explained previously, the stop surface 40*i*1 engages and/or contacts the various cam surfaces 60*e*1–60*e*8 of the cam wheel 60. Thus, the stop surface 40*i*1 serves to adjust the depth of the lancet needle based upon the position of the cam wheel 60, as will be described later on. As will be explained more clearly later on, the projection 40*i* is configured to slide within a recess 70*e* of the inner sleeve 70 when the back cap 80 is moved from the positions shown in FIGS. 1 and 5. An elongated through slot 40*f* is arranged on the cylindrical section 40*d*. As discussed above, this slot 40*f* is sized and configured to receive projections 100*m* and 110*m* of the body parts 100 and 110. In this regard, the width of the slot 40*f* can be approximately 0.16" while the length SL of the slot 40*f* can be approximately 0.74". The slot 40*f* also has rounded ends whose radius SR can be approximately 0.08". The diameter of shoulder 40*e* may be approximately 0.42".

As discussed above, continuous recess or indentation 40*h* is sized and configured to receive a projection 90*d* of the end plug 90. In this regard, the recess 40*h* may have a radius of approximately 0.007" and a depth of approximately 0.004". As can be seen in FIG. 1, diameter 90*c* of the end plug 90 is configured to slide into opening 40*g* of end 40*b*. Once the projection 90*d* engages recess 40*h*, the end plug 90 is secured to the rear portion 40 of holding member 30/40. As explained previously, surface 90*b* of the end plug 90 serves to engage or contact one end of spring S2. The end plug 90 is installed once springs S1 and S2 are arranged within the openings 30*f* and 40*l*.

FIGS. 11A-E show various views of the cam wheel 60. The cam wheel 60 can preferably be made as one-piece structure by e.g., injection molding. In this regard, it is preferably made of a plastic or synthetic resin such as, e.g., ABS plastic. The cam wheel 60 may also have be made of ABS—Dark Blue and have a finish designated as MT-11040. Additionally, the cam wheel 60 may have an overall diameter that is approximately 0.71". Of course, other materials and/or finishes may be utilized, without leaving the scope of the invention. Moreover, the cam wheel 60 may even be made of a plurality of sections of parts which are joined together to form the complete cam wheel 60, without leaving the scope of the invention.

The cam wheel 60 preferably has an outer circumferential surface 60*e* that includes indicia I which may be numbers, e.g., numbers 1–8, or letters. Of course, any desired indicia may be utilized. This indicia I can be, e.g., pad printed or silk screen raised numbers in white ink. The height of the indicia I can be approximately 0.09". A centrally disposed opening 60*j* extends through the cam disk 60. The opening 60*j* may have a diameter of approximately 0.36". As explained previously, the opening 60*j* is sized and configured to rotate around and/or about surface 40*d*. Surface 40*d* also slides within opening 60*j* when holding member 30/40 moves within lancet device LD. The cam wheel 60 also includes an enlarged diameter opening 60*k* that is defined by annular cam surfaces 60*e*1–60*e*8 and annular shoulder 60*a*. The diameter of the cylindrical surface 60*c* is sized to rotate (with a clearance) within the circular bearing recess formed by projecting walls 100*h* and 110*h*. The cam wheel 60 includes a plurality of cam surfaces 60*e*1–60*e*8 formed on a cam section 60*e*. As can be partially seen in FIG. 11B, the cam surfaces 60*e*1–60*e*8 are all spaced from edge 60*a* by different amounts. As was explained previously, these surfaces 60*e*1–8 are configured to be contacted by stop surface 40*i*1 of the holding member 30/40. Thus, for example, when contact is made between stop surface 40*i*1 and surface 60*e*1, the lancet needle will penetrate to its deepest setting. On the other hand, when contact is made between stop surface 40*i*1 and surface 60*e*8, the lancet needle will penetrate to its shallowest setting. Of course, surfaces 60*e*2–60*e*7 will set the penetrating depth in between these extreme settings. Although, the cam wheel 60 is configured with eight settings (designated by the number of cam surfaces and the indicia), the cam wheel 60 can have any number of desired settings that can range from two to as many as 20 or more, if desired. The distance or width "w1" can be approximately 0.16" whereas the width "w2" can be approximately 0.33".

A cylindrical recess 60*i* is formed between end 60*b* and annular surface 60*f*. The recess surface 60*i* is sized to rotate (with a clearance) within the circular bearing recess formed by projecting walls 100*i* and 110*i*. The cam wheel 60 also includes a plurality of angled and/o undulating surfaces 60*b*1 which form pointed tips 60*b*2. As was explained previously, these surfaces 60*b*1 engage with projection or pawl 100*p* and served to temporarily retain the cam wheel 60 in a desired set-depth position. A plurality of raised textured portions 60*h* are arranged between the indicia I. These allow the user to more easily grip the cam wheel 60 so as to cause its rotation. As was described with regard to FIG. 8, the cam wheel 60 partially projects through slot 110*p*.

Figure 11E:
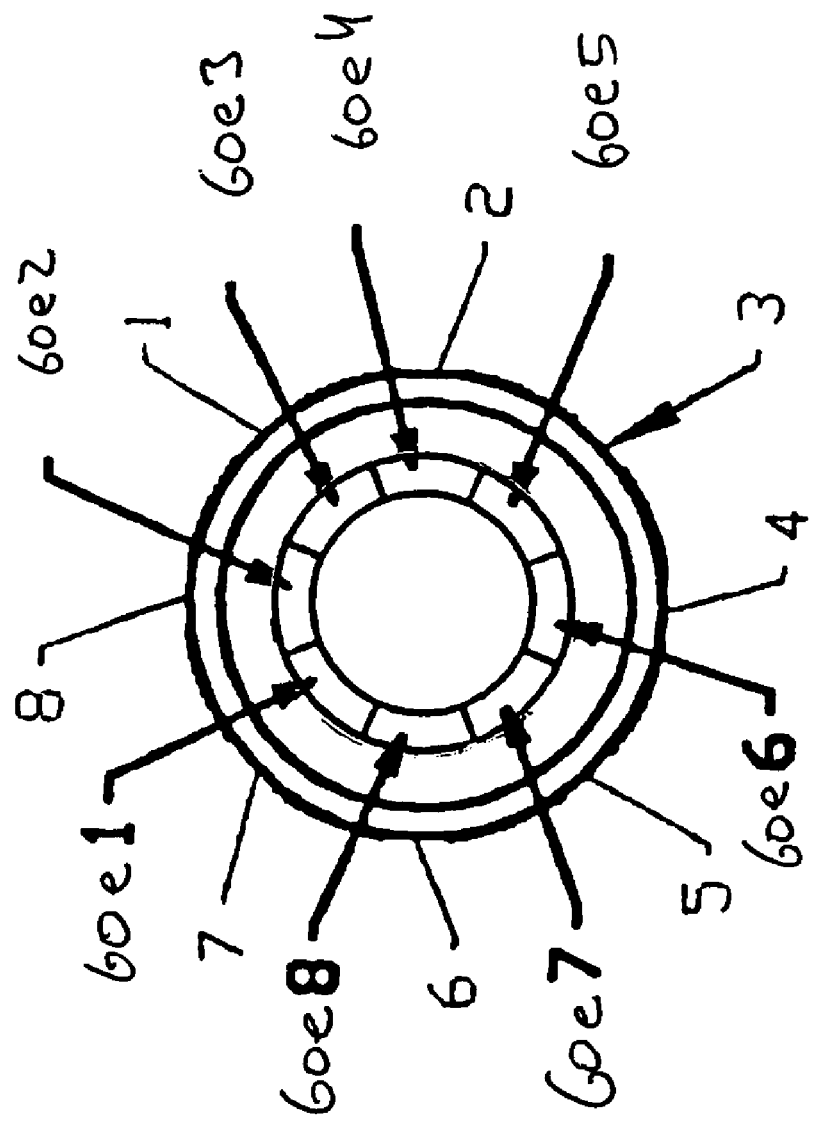
FIG. 11E shows a rear view of the cam wheel in which the cam surfaces and the indicia can be arranged.

With reference to FIG. 11E, it can be seen that indicia numbers 1–8 can be arranged to correspond to the annular cam surfaces 60*e*1–60*e*8 based upon the position of projection 40*i*. Although FIG. 11E shows one possible arrangement, it should be noted that the cam surfaces 60*e*1–60*e*8 can be arranged in any desired arrangement relative to the indicia and stop projection 40*i*, provided that the correct cam surface corresponds to the desired indicia setting.

Figure 12A:
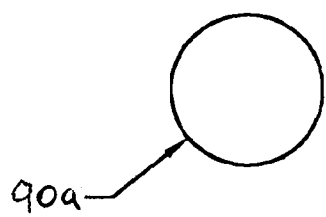
FIG. 12A shows a rear view of the end plug shown in FIG. 1.
Figure 12B:
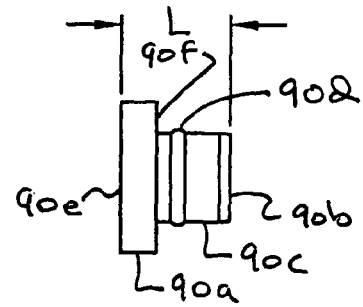
FIG. 12B shows a side view of the end plug shown in FIG. 1.
Figure 12C:
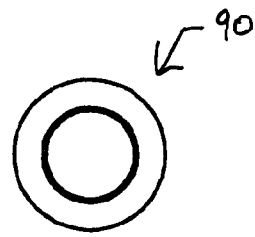
FIG. 12C shows a front view of the end plug shown in FIG. 12B.

FIGS. 12A–C show various views of the end plug 90. The end plug 90 can preferably be made as one-piece structure by e.g., injection molding. In this regard, it is preferably made of a plastic or synthetic resin such as, e.g., Delrin plastic. The end plug 90 may also be made of Delrin—Natural and have a finish designated as SPI-C1. Additionally, the end plug 90 may have an overall length L that is approximately 0.31" (i.e., between edges 90*e* and 90*b*). Of course, other materials and/or finishes may be utilized, without leaving the scope of the invention. Moreover, the end plug 90 may even be made of a plurality of sections of parts which are joined together to form the complete end plug 90, without leaving the scope of the invention.

The end plug 90 preferably has a rear planar wall 90e and a front planar wall 90b. A shoulder 90f is arranged between surfaces 90e and 90b. The diameter of cylindrical surface 90a can be approximately 0.42". The diameter of cylindrical surface 90c can be sized to slide into opening 40g. A projection 90d extends from surface 90c and is configured to engage recess 40h. The projection 90d may have a radius of 0.007" and may extend from surface 90f by approximately 0.004". End 90b can also have a chamfer that extends from surface 90c.

Figure 13A:
FIG. 13A shows a side view of the first spring shown in FIG. 1.
Figure 13B:
FIG. 13B shows an end view of the first spring shown in FIG. 13A.

FIGS. 13A–B show various views of the plunger spring S1. The spring S1 is preferably be made as one-piece structure. In this regard, it is preferably made of 0.05 mm wire. The spring S1 may also have be made of stainless steel 0.05 mm wire. Additionally, the spring S1 may have an overall freelength of approximately 36.7 mm and an outer diameter of approximately 6.2 mm. In this way, the spring S1 will be able to move freely within openings 30f and 40l. Of course, other materials may be utilized, without leaving the scope of the invention.

Figure 14A:
FIG. 14A shows a side view of the second spring shown in FIG. 1.
Figure 14B:
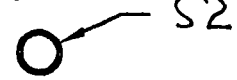
FIG. 14B shows an end view of the second spring shown in FIG. 14A.

FIGS. 14A–B show various views of the return spring S2. The spring S2 is preferably be made as one-piece structure. In this regard, it is preferably made of 0.05 mm wire. The spring S2 may also have be made of stainless steel 0.05 mm wire. Additionally, the spring S2 may have an overall freelength of approximately 25.5 mm and an outer diameter of approximately 6.2 mm. In this way, the spring S2 will be able to move freely within opening 40l. Of course, other materials may be utilized, without leaving the scope of the invention.

Figure 15A:
FIG. 15A shows a side view of the third spring shown in FIG. 1.
Figure 15B:
FIG. 15B shows an end view of the third spring shown in FIG. 15A.
Figure 16D:
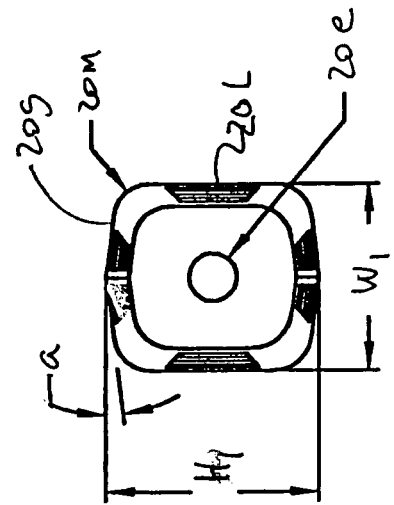
FIG. 16D shows a top view of the front cap shown in FIG. 16A.
Figure 16E:
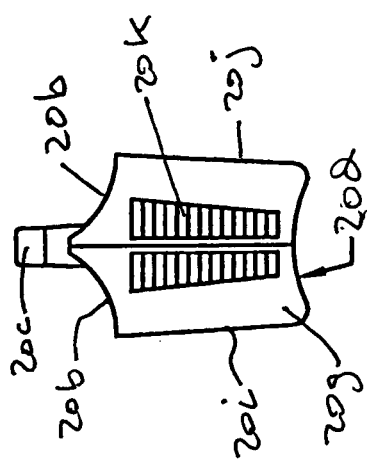
FIG. 16E shows a front end view of the front cap shown in FIG. 16C.
Figure 16C:
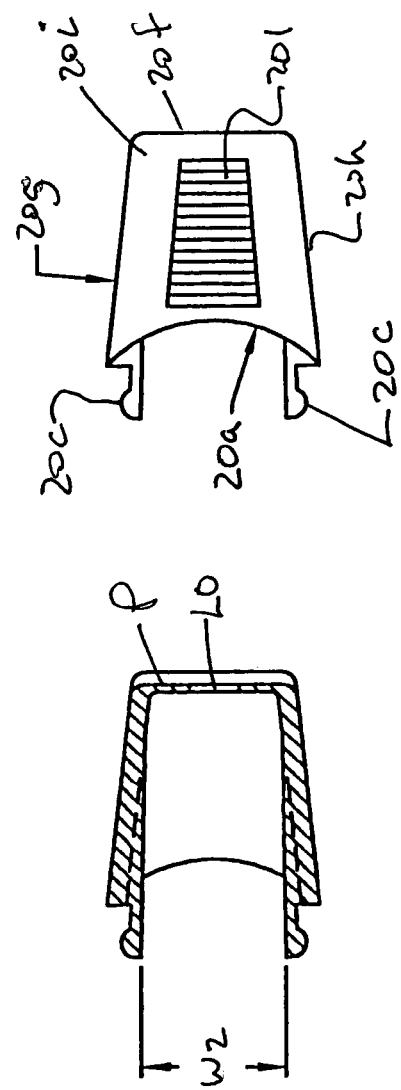
FIG. 16C shows a side view of the front cap of the lancet device shown in FIG. 16C.
Figures 16A, 16B:
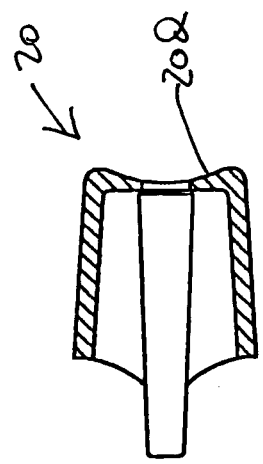
FIG. 16A shows a top cross-section view of the front cap of the lancet device shown in FIG. 1.
FIG. 16B shows a side cross-section view of the front cap of the lancet device shown in FIG. 1.

FIGS. 15A–B show various views of the cocking spring S3. The spring S3 is preferably be made as one-piece structure. In this regard, it is preferably made of 0.025 mm wire. The spring S3 may also have be made of stainless steel 0.025 mm wire. Additionally, the spring S3 may have an overall freelength of approximately 13.6 mm and an outer diameter of approximately 10.1 mm. In this way, the spring S3 will be able to move freely over surface 40d and projections 40i, 40j and 40k. Of course, other materials may be utilized, without leaving the scope of the invention.

FIGS. 16A–E show various views of the front cover 20. The front cover 20 can preferably be made as one-piece structure by e.g., injection molding. In this regard, it is preferably made of a plastic or synthetic resin such as, e.g., ABS plastic. The front cover 20 may also be made of ABS—Light Blue and have a finish designated as SPI-A2. Additionally, the front cover 20 may have an overall length that is approximately ¾" (i.e., between left end of projection 20c and end 20f). Of course, other materials and/or finishes may be utilized, without leaving the scope of the invention. Moreover, the front cover 20 may even be made of a plurality of sections of parts which are joined together to form the complete front cover 20, without leaving the scope of the invention.

The front cover 20 preferably has a front wall 20f that includes a circular and/or curved indentation 20d (i.e., defining plane P) and a centrally disposed through opening 20e (i.e., defining lancet opening LO). The radius of this indentation 20d may be approximately ⅜" and the diameter of the through opening 20e may be approximately 0.13". Of course, the invention also contemplates a plane P which is straight or which curves outwardly (not shown). As was described previously, the left edges 20c are configured to slide into front edges 100a and 110a until contact occurs between circular and/or curved edges 20b and edges 100a1 and 110a1. The projections 20c may have a radius of approximately 0.02". As explained previously, these projections 20c are configured to engage with the recesses 100a2 and 110a2 (see FIGS. 7A and 8C).

Side walls 20g and 20h are preferably tapered inwardly from edge 20a to surface 20d and may form rounded corners (e.g., with a radius of approximately 0.1") where walls 20g and 20h meets wall 20d. Walls 20g and 20h can also be curved along their length (see FIG. 16C), having a radius of approximately 30", and may also be curved outwardly (i.e., convex, see FIG. 16C). Side walls 20g and 20h may further be formed of tapered surfaces which meet at a center (see FIG. 16E). These surfaces may tapered outwards from a center at an angle "a" of approximately 7 degrees. Rounded corners 20m (e.g., with a radius of approximately 0.1") are provided between walls 20g–j. The width "w1" of the front cap 20 can be approximately ½" while the height H1 can be approximately 0.56" (see FIG. 16E). Walls 20g and 20h can also include raised and/or textured surfaces 20k which allow a user to more easily grip the front cap 20, thus facilitating its removal. Similarly, walls 20i and 20j can also include raised and/or textured surfaces 20l which allow a user to more easily grip the front cap 20. The width "w2" of the front cap 20 can be approximately 0.38" and can taper inwards by about 1 degree per side towards end 20d.

FIGS. 17A–G show various views of the trigger 50. The trigger 50 can preferably be made as one-piece structure by e.g., injection molding. In this regard, it is preferably made of a plastic or synthetic resin such as, e.g., ABS plastic. The trigger 40 may also be made of ABS—Red and have a finish designated as SPI-A2. Additionally, the trigger 50 may have an overall length that is approximately 1.1". Of course, other materials and/or finishes may be utilized, without leaving the scope of the invention. Moreover, the trigger 50 may even be made of a plurality of sections of parts which are joined together to form the complete trigger 50, without leaving the scope of the invention.

The trigger 50 preferably has a rear end that includes a rounded projection 50d. This rounded projection 50d is configured to contact an inner surface of body parts 100 and 110 (see FIG. 1), and serves to brace or counter the movement of the trigger 50 when the trigger 50 is pressed into the lancet device (See FIG. 2). The projection 50d may have a radius of approximately 0.03". The trigger 50 also has front end 50b that includes a rounded projection 50e. This rounded projection 50e is configured to contact surface 30c2 of deflecting member 30c of the holding member 30/40 (see FIG. 9) upon movement of the trigger 50, when the trigger 50 is pressed into the lancet device. The projection 50e may have a radius of approximately 0.03". The trigger 50 also includes a connecting member 50g which connects the push button 50a to the support 50f. Two shaft members or journals 50c project from opposite sides of the support 50f. The journals 50c may have a diameter of approximately 0.06" and the width "w1" may be 0.36". These journals 50c also have rounded ends whose radius can be approximately 0.03". As explained previously, these journals 50c are configured to be mounted in the bearing supports formed by projections 100j and 110j. In this regard, the openings formed by these projections 100j and 110j should be sized to be the same or slightly larger than the diameter of journals 50c. In this way, the journals 50c can fit snugly in the supports 100j/110j. The width (measured in the direction of FIG. 17E) of the support 50f may be approximately 0.1".

The push button 50a preferably has a tear-drop shape and includes an inwardly curved (i.e., concave) surface that has a radius of approximately 1.9". A lip member 50b projects from the front of the push button 50a. This lip member 50b is approximately 0.06" wide and may extend from the push button 50*a* by approximately 0.04". The thickness T2 of the lip member 50*b* (measured in the direction of FIG. 17F) can be approximately 0.02" and the distance T1 can be approximately 0.04". Angle "x" can be approximately 5 degrees and angle "y" can be approximately 18 degrees. The lip member 50*b* limits the upward movement of the push button 50*a* by contacting an inner surface of the body parts 100 and 110 when the trigger 50 is in the original non-deflected position (see e.g., FIG. 1). The push button 50*a* can have a width "w2" of approximately 0.25". The length L1 can be approximately 0.51" while the length L2 can be approximately 0.57". Finally, the curved surface 50*a* can also include a texture (see FIG. 17G) formed of projections and recesses to prevent a user's finger from slipping off of the button 50*a*.

As explained above with regard to FIG. 1, the trigger 50 is designed to preferably deflect inwardly when a user pushes against the push button 50*a* (see FIG. 2) and to return to an original position (see FIG. 1 or 3). In this regard, the deflection occurs in the area between journals 50*c* and connecting element 50*g* and/or possibly somewhat between projection 50*d* and journals 50*c*. The design is such that the material properties of the trigger 50 allows it to act like a natural spring.

FIGS. 18A–E show various views of the back cap 80. The back cap 80 can preferably be made as one-piece structure by e.g., injection molding. In this regard, it is preferably made of a plastic or synthetic resin such as, e.g., ABS plastic. The back cap 80 may also be made of ABS—Light Blue and have a finish designated as SPI-A2. Additionally, the back cap 80 may have an overall length L2 that is approximately 0.9" (i.e., between ends 80*a* and 80*b*). Of course, other materials and/or finishes may be utilized, without leaving the scope of the invention. Moreover, the back cap 80 may even be made of a plurality of sections of parts which are joined together to form the complete back cap 80, without leaving the scope of the invention.

The back cap 80 preferably has a rear wall 80*b* that has a planar outer surface and a planar inner surface 80*d*. The back cap 80 also has an opening 80*e* that extends from end 80*a* to surface 80*d*. This opening 80*e* is generally rectangular and has a width "w1" of approximately 0.49" and a width "w2" of approximately 0.66". This opening 80*e* extends from edge 80*a* and tapers inwardly towards surface 80*d* at an angle of approximately 1 degrees (per side). The width "w3" between outer surfaces 80*i* and 80*h* may be approximately 0.53" and may taper outwardly from edge 80*a* to shoulder 80*c* by approximately 1 degree per side. The width "w4" between outer surfaces 80*f* and 80*g* may be approximately 0.72" and may taper outwardly from edge 80*a* to shoulder 80*c* by approximately 1 degree per side. The length L1 from end 80*b* to shoulder 80*c* may be approximately 0.49". The walls 80*f*–80*i* are configured to slide into rear ends 100*b* and 110*b* until contact occurs between the shoulder 80*c* and edges 100*b* and 110*b*. As will be explained later on with regard to FIG. 19, the back cap 80 and specifically opening 80*e*, is configured to receive or otherwise engage with the inner sleeve 70. Although not shown, a recess and projection connection may be utilized between the sleeve 70 and back cap 80. Of course, other connecting mechanisms, whether conventional or otherwise, may also be utilized in place of the projection and recess connection such as, e.g., a friction fit connection and/or adhesive attachment.

Side walls 80*j*, 80*k*, 80*l* and 80*m* may also taper and/or curve from the top of shoulder 80*c* to surface 80*b*. The approximately square shaped surface 80*b* may have a width "w5" of approximately 0.84 and a width "w6" of approximately 0.66". In this regard, walls 80*j*–80*m* may also have a radius of approximately 1.44" and may be outwardly curved, i.e., concave. Walls 80*l* and 80*m* may also have textured surfaces 80*n* and the walls 80*j* and 80*k* may have a textured surface 80*q*. As can be seen in FIG. 18B, walls 80*l* and 80*m* may be formed by tapered surfaces that meet at the center and which have an angle "a" of approximately of 7 degrees.

FIGS. 19A–C show various views of the inner sleeve 70. The inner sleeve 70 can preferably be made as one-piece structure by e.g., injection molding. In this regard, it is preferably made of a plastic or synthetic resin such as, e.g., ABS plastic. The inner sleeve 70 may also be made of ABS—Light Blue and have a finish designated as SPI-C1. Additionally, the inner sleeve 70 may have an overall length L that is approximately 0.6" (i.e., between edges 70*a* and 70*b*). Of course, other materials and/or finishes may be utilized, without leaving the scope of the invention. Moreover, the inner sleeve 70 may even be made of a plurality of sections of parts which are joined together to form the complete inner sleeve 70, without leaving the scope of the invention.

The inner sleeve 70 has a front wall 70*a* that has a planar outer surface and a planar inner surface 70*d*. An opening 70*c* is provided in the wall 70*a*. This opening 70*c* has a circular central part and a generally polygonal recess 70*e*. Recess 70*e* is approximately 0.05" wide. As was previously explained, the recess 70*e* is sized and configured to receive projection 40*i*. The inner sleeve 70 is able slide over the rear portion 40 (from the front) of the holding member 30/40 when the lancet device is assembled.

Surfaces 70*f*–70*i* are preferably tapered to match the tapered inner surfaces of opening 80*e*. In this way, when the sleeve 70 is inserted into back cap 80, the shoulder 70*j* will abut edge 80*a* of the back cap 80. The width "w1" can be approximately 0.42". The width "w2" can be approximately 0.53". The width "w3" can be approximately 0.65". Finally, the width "w4" can be approximately 0.72". The walls 70*h* and 70*i* can taper from walls 70*f* and 70*g* by an angle "a" of approximately 7 degrees from a center position (see FIG. 19B).

All the parts of the lancet device, with the exception of the springs S1-S3 (which can be made of spring steel) and with the exception of the lancet needle (which can be a conventional metal needle mounted to a conventional plastic lancet 10), may be made from plastic materials and can be formed using conventional injection molding techniques or other known manufacturing methods. The cam disk for example can be integrally formed with peripheral grooves and/or projections (similar to a coin), and with the indicating marks. However, when practical, other materials and manufacturing processes may also be utilized.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A lancet device, comprising:
a body comprising a side opening arranged between front and rear ends of the body;
a trigger;
a front cover comprising a skin engaging end that includes a lancet opening through which a lancet needle extends;
a holding member movably mounted within the body and comprising a front end and a rear end;
the front end being configured to receive a lancet;
a stop surface that moves with the holding member;
a cam wheel comprising cam surfaces which can be contacted by the stop surface; and
the cam wheel being configured to rotate at least partially about an axis that is at least substantially parallel to an axis running through at least one of the lancet opening and the holding member,
wherein a portion of the cam wheel projects out from the side opening.

2. The lancet device of claim 1, further comprising a back cap configured to move between a retracted position and an original position.

3. The lancet device of claim 2, wherein the back cap is configured to move the holding member to a retracted position.

4. The lancet device of claim 2, wherein the back cap is coupled to a surface that engages the rear end of the holding member.

5. The lancet device of claim 2, wherein the back cap is coupled to an inner sleeve that includes a surface that engages the rear end of the holding member.

6. The lancet device of claim 5, wherein the inner sleeve comprises an opening that receives a rear end of the holding member.

7. The lancet device of claim 2, wherein the back cap is coupled to in inner sleeve that includes a surface that engages projections disposed on the rear end of the holding member.

8. The lancet device of claim 2, further comprising a spring for biasing the back cap towards an original position.

9. The lancet device of claim 1, further comprising a first spring for biasing the holding member towards an extended position and a second spring for biasing the holding member in an opposite direction.

10. The lancet device of claim 9, wherein the first spring contacts one side of a projection extending inwardly from the body and wherein the second spring contacts another side of the projection.

11. The lancet device of claim 10, further comprising an end plug mounted to the rear end of the holding member.

12. The lancet device of claim 11, wherein the first spring is disposed between the projection and an inner wall surface arranged in the area of the front end of the holding member and wherein the second spring is disposed between the projection and the end plug.

13. The lancet device of claim 1, wherein the trigger is movably mounted to the body.

14. The lancet device of claim 1, wherein the front cover is removably mounted to the body.

15. The lancet device of claim 1, wherein the holding member comprises a projection that includes the stop surface.

16. The lancet device of claim 1, wherein the holding member comprises an integrally formed projection that includes the stop surface.

17. The lancet device of claim 1, wherein the front end comprises an opening that is configured to removably receive the lancet.

18. The lancet device of claim 1, further comprising a deflecting member configured to be deflected by the trigger.

19. The lancet device of claim 18, wherein the deflecting member is coupled to the holding member.

20. The lancet device of claim 18, wherein the deflecting member comprises a first stop surface that contacts a first surface of a holding projection extending inwardly from the body.

21. The lancet device of claim 20, wherein the deflecting member is integrally formed with the holding member.

22. The lancet device of claim 1, wherein the cam wheel comprises indicia.

23. The lancet device of claim 22, wherein the cam surfaces are arranged on an annular cam section of the cam wheel and wherein the indicia is arranged on an outer circumferential surface of the cam wheel.

24. The lancet device of claim 1, wherein the cam wheel comprises a centrally disposed opening that is mounted about the holding member.

25. The lancet device of claim 24, wherein the holding member comprises a front portion that includes the front end and a rear portion that includes the rear end, wherein the front and rear portions are connected together.

26. The lancet device of claim 24, wherein the rear portion comprises a slot which at least partially receives a projection that extends from the body.

27. The lancet device of claim 1, wherein the cam wheel rotates about an axis that runs through the lancet opening and the holding member.

28. The lancet device of claim 1, wherein the cam wheel is disposed between the trigger and a back cap.

29. The lancet device of claim 1, wherein the body comprises a two-piece body.

30. The lancet device of claim 29, wherein the cam wheel is axially retained between walls of the two-piece body.

31. The lancet device of claim 30, wherein the front cover is removably mounted to the two-piece body.

32. The lancet device of claim 31, further comprising a back cap movably mounted to the two-piece body.

33. The lancet device of claim 1, wherein the body comprises two oppositely arranged curved side indentations.

34. The lancet device of claim 1, wherein the side opening constitutes a mechanism for viewing indicia of the cam wheel.

35. The lancet device of claim 34, wherein the mechanism for viewing indicia of the cam wheel comprises a slot.

36. The lancet device of claim 1, further comprising a ratchet pawl which engages an annular undulating surface of the cam wheel, whereby the cam wheel is maintained at a desired set-depth position.

37. A method of puncturing a surface of skin using the lancet device of claim 1, the method comprising:
adjusting a set depth of penetration of the needle by rotating the cam wheel to a desired set position;
disposing the skin engaging end of the lancet device against a user's skin; and
triggering the trigger to cause the lancet needle to penetrate the user's skin,
wherein the puncture allows a blood sample to be taken.

38. A method of using the lancet device of claim 1, the method comprising:

rotating the cam wheel to a desired set position;
moving the holding member to a retracted position;
maintaining the holding member in the retracted position until the trigger is triggered;
disposing the skin engaging end of the lancet device against a user's skin; and
triggering the trigger to cause movement of the holding member.

39. A lancet device, comprising:
a body:
a tripper:
a front cover comprising a skin engaging end that includes a lancet opening through which a lancet needle extends;
a holding member movably mounted within the body and comprising a front end and a rear end;
the front end being configured to receive a lancet;
a stop surface that moves with the holding member;
a cam wheel comprising cam surfaces which can be contacted by the stop surface;
the cam wheel being configured to rotate at least partially about an axis that is at least substantially parallel to an axis running through at least one of the lancet opening and the holding member, and
a first spring for biasing the holding member towards an extended position and a second spring for biasing the holding member in an opposite direction,
wherein the first and second springs are arranged within an axial opening of the holding member.

40. A lancet device, comprising:
a body;
a trigger;
a front cover comprising a skin engaging end that includes a lancet opening through which a lancet needle extends;
a holding member movably mounted within the body and comprising a front end and a rear end;
the front end being configured to receive a lancet;
a stop surface that moves with the holding member;
a cam wheel comprising cam surfaces which can be contacted by the stop surface;
the cam wheel being configured to rotate at least partially about an axis that is at least substantially parallel to an axis running through at least one of the lancet opening and the holding member;
a first spring for biasing the holding member towards an extended position and a second spring for biasing the holding member in an opposite direction, and
the first spring contacting one side of a protection extending inwardly from the body and the second spring contacting another side of the projection,
wherein the projection extends into an elongated slot formed in the holding member.

41. A lancet device, comprising:
a body;
a trigger;
a front cover comprising a skin engaging end that includes a lancet opening through which a lancet needle extends;
a holding member movably mounted within the body and comprising a front end and a rear end;
the front end being configured to receive a lancet;
a stop surface that moves with the holding member;
a cam wheel comprising cam surfaces which can be contacted by the stop surface;
the cam wheel being configured to rotate at least partially about an axis that is at least substantially parallel to an axis running through at least one of the lancet opening and the holding member and comprising a centrally disposed opening that is mounted about the holding member; and
the rear portion comprising a slot which at least partially receives a projection that extends from the body,
wherein the front portion comprises a deflecting member configured to be deflected by the trigger.

42. A lancet device, comprising:
a body;
a trigger;
a front cover comprising a skin engaging end that includes a lancet opening through which a lancet needle extends;
a holding member movably mounted within the body and comprising a front end and a rear end;
the front end being configured to receive a lancet;
a stop surface that moves with the holding member;
a cam wheel comprising cam surfaces which can be contacted by the stop surface; and
the cam wheel being configured to rotate at least partially about an axis that is at least substantially parallel to an axis running through at least one of the lancet opening and the holding member,
wherein the body comprises at least one curved side indentation through which the cam wheel protrudes.

43. A lancet device, comprising:
a body;
a trigger;
a front cover comprising a skin engaging end that includes a lancet opening through which a lancet needle extends;
a holding member movably mounted within the body, the holding member comprising a front end and a rear end;
the front end being configured to receive a lancet;
a stop projection coupled to the holding member; and
a cam wheel comprising indicia and annular cam surfaces which can be contacted by the stop projection;
the cam wheel being configured to rotate at least partially;
each annular cam surface of the cam wheel being contacted by the stop protection when each annular cam surface is located in a predetermined position,
wherein the cam wheel is axially retained between walls of the body.

44. A lancet device, comprising:
a body;
a trigger;
a front cover comprising a skin engaging end that includes a lancet opening through which a lancet needle extends;
a holding member movably mounted within the body, the holding member comprising a front end and a rear end;
the front end being configured to receive a lancet;
a back cap configured to move the holding member to a retracted position;
a stop surface coupled to the holding member;
a cam wheel at least partially arranged within the body;
the cam wheel comprising indicia and annular cam surfaces which can be contacted by the stop projection; and
the cam wheel being configured to rotate at least partially,
each annular cam surface of the cam wheel being contacted by the stop projection when each annular cam surface is located in a predetermined position,
wherein the cam wheel protrudes from at least one side wall of the body.

* * * * *

UNITED STATES PATENT AND TRADEMARK OFFICE
CERTIFICATE OF CORRECTION

| | | |
|---|---|---|
| PATENT NO. | : 7,105,006 B2 | Page 1 of 1 |
| APPLICATION NO. | : 10/641101 | |
| DATED | : September 12, 2006 | |
| INVENTOR(S) | : Steven Schraga | |

It is certified that error appears in the above-identified patent and that said Letters Patent is hereby corrected as shown below:

Title Page, Item (12) "Shraga" should be -- Schraga --.

On the title page of the printed patent, at Item (75), Inventor "Steven Shraga, Surfside, FL (US)"

should be "Steven Schraga, Surfside, FL (US)"

Signed and Sealed this
Tenth Day of April, 2012

David J. Kappos
*Director of the United States Patent and Trademark Office*